(12) United States Patent
Davis

(10) Patent No.: US 7,132,415 B2
(45) Date of Patent: *Nov. 7, 2006

(54) METHODS AND THERAPEUTIC COMBINATIONS FOR THE TREATMENT OF XANTHOMA USING STEROL ABSORPTION INHIBITORS

(75) Inventor: Harry R. Davis, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 228 days.

This patent is subject to a terminal disclaimer.

(21) Appl. No.: 10/247,095

(22) Filed: Sep. 19, 2002

(65) Prior Publication Data

US 2003/0119809 A1    Jun. 26, 2003

Related U.S. Application Data

(60) Provisional application No. 60/323,942, filed on Sep. 21, 2001.

(51) Int. Cl.
  *A61K 31/395*   (2006.01)
  *A61K 31/70*    (2006.01)
  *A61K 38/43*    (2006.01)

(52) U.S. Cl. .................. 514/210.02; 514/210; 514/23; 424/94.1

(58) Field of Classification Search ............... 424/94.1; 514/210.02, 210, 23
See application file for complete search history.

(56) References Cited

U.S. PATENT DOCUMENTS

| | | |
|---|---|---|
| 2,809,194 A | 10/1957 | Novello |
| 3,108,097 A | 10/1963 | Ugi |
| 3,152,173 A | 10/1964 | Ehrhart |
| 3,267,104 A | 8/1966 | Hermans |
| 3,399,192 A | 8/1968 | Regnier |
| 3,692,895 A | 9/1972 | Nelson |
| 3,716,583 A | 2/1973 | Nakamura |
| 3,781,328 A | 12/1973 | Witte |
| 3,948,973 A | 4/1976 | Phillips |
| 4,072,705 A | 2/1978 | Mieville |
| 4,075,000 A | 2/1978 | Abdulla |
| 4,144,232 A | 3/1979 | Koppel |
| 4,148,923 A | 4/1979 | Giudicelli |
| 4,166,907 A | 9/1979 | Krapcho |
| 4,178,695 A | 12/1979 | Erbeia |
| 4,179,515 A | 12/1979 | Mieville |
| 4,235,896 A | 11/1980 | Mieville |
| 4,239,763 A | 12/1980 | Milavec |
| 4,250,191 A | 2/1981 | Edwards |
| 4,260,743 A | 4/1981 | Bose |
| 4,304,718 A | 12/1981 | Kamiya |
| 4,375,475 A | 3/1983 | Willard |
| 4,443,372 A | 4/1984 | Luo |
| 4,444,784 A | 4/1984 | Hoffman |
| 4,472,309 A | 9/1984 | Kamiya |
| 4,479,900 A | 10/1984 | Luo |
| 4,500,456 A | 2/1985 | Spitzer |
| 4,534,786 A | 8/1985 | Luo |
| 4,564,609 A | 1/1986 | Tamura |
| 4,567,195 A | 1/1986 | Schwarz |
| 4,576,748 A | 3/1986 | Greenlee |
| 4,576,749 A | 3/1986 | Zahler |
| 4,576,753 A | 3/1986 | Kamiya |
| 4,581,170 A | 4/1986 | Mueller |
| 4,595,532 A | 6/1986 | Miller |
| 4,602,003 A | 7/1986 | Malinow |
| 4,602,005 A | 7/1986 | Malinow |
| 4,614,614 A | 9/1986 | Ernest |
| 4,616,047 A | 10/1986 | Lafon |
| 4,620,867 A | 11/1986 | Luo |
| 4,626,549 A | 12/1986 | Molloy |
| 4,633,017 A | 12/1986 | Mueller |
| 4,642,903 A | 2/1987 | Davies |
| 4,654,362 A | 3/1987 | Lommen |
| 4,675,399 A | 6/1987 | Miller |
| 4,680,289 A | 7/1987 | Applezweig |
| 4,680,391 A | 7/1987 | Firestone |
| 4,687,777 A | 8/1987 | Meguro et al. |
| 4,739,101 A | 4/1988 | Bourgogne |
| 4,778,883 A | 10/1988 | Yoshioka |
| 4,784,734 A | 11/1988 | Torii |
| 4,794,108 A | 12/1988 | Kishimoto |
| 4,800,079 A | 1/1989 | Boyer |
| 4,803,266 A | 2/1989 | Kawashima |
| 4,814,354 A | 3/1989 | Ghebre-Sellassie |
| 4,834,846 A | 5/1989 | Abramson |
| 4,871,752 A | 10/1989 | Zermatter |
| 4,876,365 A | 10/1989 | Kirkup |
| 4,879,301 A | 11/1989 | Umio |
| 4,895,726 A | 1/1990 | Curtet |
| 4,925,672 A | 5/1990 | Gremm |

(Continued)

FOREIGN PATENT DOCUMENTS

BE    884722 A    12/1980

(Continued)

OTHER PUBLICATIONS

U.S. Appl. No. 10/057,534, filed Jan. 25, 2002, Harry R. Davis et al.

(Continued)

*Primary Examiner*—Vickie Kim
(74) *Attorney, Agent, or Firm*—Mark W. Russell; Ann Marie Cannoni

(57) ABSTRACT

The present invention provides therapeutic combinations and methods including at least one sterol or 5α-stanol absorption inhibitor that can be useful for treating xanthomas.

2 Claims, No Drawings

U.S. PATENT DOCUMENTS

| | | |
|---|---|---|
| 4,937,267 A | 6/1990 | Holloway |
| 4,939,248 A | 7/1990 | Yoshioka |
| 4,952,689 A | 8/1990 | Kawashima |
| 4,961,890 A | 10/1990 | Boyer |
| 4,983,597 A | 1/1991 | Yang |
| 4,990,535 A | 2/1991 | Cho |
| 5,021,461 A | 6/1991 | Robinson et al. |
| 5,030,628 A | 7/1991 | Joyeau |
| 5,073,374 A | 12/1991 | McCarty |
| 5,091,525 A | 2/1992 | Brennan |
| 5,093,365 A | 3/1992 | Berge |
| 5,099,034 A | 3/1992 | Yoshida |
| 5,100,675 A | 3/1992 | Cho |
| 5,106,833 A | 4/1992 | Broze |
| 5,110,730 A | 5/1992 | Edgington |
| 5,112,616 A | 5/1992 | McCarty |
| 5,120,713 A | 6/1992 | Mugica |
| 5,120,729 A | 6/1992 | Chabala |
| 5,130,333 A | 7/1992 | Pan |
| 5,145,684 A | 9/1992 | Liversidge |
| 5,157,025 A | 10/1992 | Aberg |
| 5,162,117 A | 11/1992 | Stupak |
| 5,178,878 A | 1/1993 | Wehling |
| 5,188,825 A | 2/1993 | Iles |
| 5,190,970 A | 3/1993 | Pan |
| 5,204,461 A | 4/1993 | Murayama |
| 5,219,574 A | 6/1993 | Wehling |
| 5,223,264 A | 6/1993 | Wehling |
| 5,229,362 A | 7/1993 | Kirst |
| 5,229,381 A | 7/1993 | Doherty |
| 5,229,510 A | 7/1993 | Knight |
| 5,260,305 A | 11/1993 | Dennick |
| 5,278,176 A | 1/1994 | Lin |
| H001286 H | 2/1994 | Eisman |
| 5,286,631 A | 2/1994 | Boeck |
| 5,298,497 A | 3/1994 | Tschollar |
| 5,306,817 A | 4/1994 | Thiruvengadam |
| 5,318,767 A | 6/1994 | Liversidge |
| 5,348,953 A | 9/1994 | Doherty |
| 5,350,868 A | 9/1994 | Yoshida |
| 5,358,852 A | 10/1994 | Wu |
| 5,384,124 A | 1/1995 | Courteille |
| 5,385,885 A | 1/1995 | Gasic |
| 5,399,363 A | 3/1995 | Liversidge |
| 5,401,513 A | 3/1995 | Wehling |
| 5,412,092 A | 5/1995 | Rey |
| 5,429,824 A | 7/1995 | June |
| 5,446,464 A | 8/1995 | Feldle |
| 5,461,039 A | 10/1995 | Tschollar |
| 5,464,632 A | 11/1995 | Cousin |
| 5,494,683 A | 2/1996 | Liversidge |
| 5,503,846 A | 4/1996 | Wehling |
| 5,510,118 A | 4/1996 | Bosch |
| 5,510,466 A | 4/1996 | Krieger |
| 5,518,187 A | 5/1996 | Bruno |
| 5,518,738 A | 5/1996 | Eickhoff |
| 5,545,628 A | 8/1996 | Deboeck |
| 5,550,229 A | 8/1996 | Iwasaki |
| 5,552,160 A | 9/1996 | Liversidge |
| 5,561,227 A | 10/1996 | Thiruvengadam |
| 5,563,264 A | 10/1996 | Kume |
| 5,567,439 A | 10/1996 | Myers |
| 5,576,014 A | 11/1996 | Mizumoto |
| 5,587,172 A | 12/1996 | Cherukuri |
| 5,587,180 A | 12/1996 | Allen |
| 5,591,456 A | 1/1997 | Franson |
| 5,593,971 A | 1/1997 | Tschollar |
| 5,595,761 A | 1/1997 | Allen |
| 5,607,697 A | 3/1997 | Alkire |
| 5,612,353 A | 3/1997 | Ewing |
| 5,612,367 A | 3/1997 | Timko |
| 5,612,378 A | 3/1997 | Tianbao |
| 5,618,707 A | 4/1997 | Homann |
| 5,622,719 A | 4/1997 | Myers |
| 5,622,985 A | 4/1997 | Olukotun |
| 5,624,920 A * | 4/1997 | McKittrick et al. .... 514/210.02 |
| 5,627,176 A | 5/1997 | Kirkup |
| 5,631,023 A | 5/1997 | Kearney |
| 5,631,365 A | 5/1997 | Rosenblum |
| 5,633,246 A | 5/1997 | McKittrick |
| 5,635,210 A | 6/1997 | Allen |
| 5,639,475 A | 6/1997 | Bettman |
| 5,639,739 A | 6/1997 | Dominguez |
| 5,656,624 A * | 8/1997 | Vaccaro et al. ........ 514/210.02 |
| 5,661,145 A * | 8/1997 | Davis .................... 514/210.02 |
| 5,674,893 A | 10/1997 | Behounek |
| 5,688,785 A | 11/1997 | Vaccaro |
| 5,688,787 A | 11/1997 | Burnett |
| 5,688,990 A | 11/1997 | Shankar |
| 5,691,375 A | 11/1997 | Behounek |
| 5,698,527 A | 12/1997 | Kim |
| 5,698,548 A | 12/1997 | Dugar |
| 5,703,188 A | 12/1997 | Mandeville |
| 5,703,234 A | 12/1997 | Iwasaki |
| 5,709,886 A | 1/1998 | Bettman |
| 5,718,388 A | 2/1998 | Czekai |
| 5,728,827 A | 3/1998 | Thiruvengadam et al. |
| 5,734,077 A | 3/1998 | Regnier |
| 5,739,321 A | 4/1998 | Wu |
| 5,744,467 A | 4/1998 | McKittrick |
| 5,747,001 A | 5/1998 | Wiedmann |
| 5,753,254 A | 5/1998 | Khan |
| 5,756,470 A | 5/1998 | Yumibe |
| 5,759,865 A | 6/1998 | Bruns |
| 5,767,115 A * | 6/1998 | Rosenblum et al. ... 514/210.02 |
| 5,776,491 A | 7/1998 | Allen |
| 5,807,576 A | 9/1998 | Allen |
| 5,807,577 A | 9/1998 | Ouali |
| 5,807,578 A | 9/1998 | Acosta-Cuello |
| 5,807,834 A | 9/1998 | Morehouse |
| 5,808,056 A | 9/1998 | Amato |
| 5,817,806 A | 10/1998 | Rossi |
| 5,827,536 A | 10/1998 | Laruelle |
| 5,827,541 A | 10/1998 | Yarwood |
| 5,831,091 A | 11/1998 | Ohmizu |
| 5,843,984 A | 12/1998 | Clay |
| 5,846,966 A | 12/1998 | Rosenblum |
| 5,847,008 A | 12/1998 | Doebber |
| 5,847,115 A | 12/1998 | Iwasaki |
| 5,851,553 A | 12/1998 | Myers |
| 5,856,473 A | 1/1999 | Shankar |
| 5,858,409 A | 1/1999 | Karetny |
| 5,859,051 A | 1/1999 | Adams |
| 5,862,999 A | 1/1999 | Czekai |
| 5,866,163 A | 2/1999 | Myers |
| 5,869,098 A | 2/1999 | Misra |
| 5,871,781 A | 2/1999 | Myers |
| 5,880,148 A | 3/1999 | Edgar |
| 5,883,109 A | 3/1999 | Gregg |
| 5,886,171 A | 3/1999 | Wu |
| 5,919,672 A | 7/1999 | Homann |
| 5,925,333 A | 7/1999 | Krieger |
| 5,952,003 A | 9/1999 | Guentensberger |
| 5,952,321 A | 9/1999 | Doherty |
| 5,959,123 A | 9/1999 | Singh |
| 5,972,389 A | 10/1999 | Shell |
| 5,976,570 A | 11/1999 | Greaves |
| 5,985,936 A | 11/1999 | Novak |
| 5,990,102 A | 11/1999 | Hickey |
| 5,994,554 A | 11/1999 | Kliewer |
| 5,998,441 A | 12/1999 | Palkowitz |
| 6,008,237 A | 12/1999 | Sahoo |
| 6,027,747 A | 2/2000 | Terracol |
| 6,028,109 A | 2/2000 | Wilson |

| | | | | | | |
|---|---|---|---|---|---|---|
| 6,030,990 | A | 2/2000 | Maeda et al. | DE | 2521113 A | 3/1976 |
| 6,033,656 | A | 3/2000 | Mikami | EP | 0002151 A1 | 5/1979 |
| 6,040,147 | A | 3/2000 | Ridker | EP | 0002151 B1 | 5/1979 |
| 6,043,257 | A | 3/2000 | Dominguez | EP | 0010299 B1 | 2/1984 |
| 6,056,975 | A | 5/2000 | Mitra | EP | 0179559 A2 | 4/1986 |
| 6,057,342 | A | 5/2000 | Fevig | EP | 0199630 A1 | 10/1986 |
| 6,063,764 | A | 5/2000 | Creasey | EP | 0264231 A1 | 4/1988 |
| 6,066,653 | A | 5/2000 | Gregg | EP | 0266896 B1 | 5/1988 |
| 6,071,899 | A | 6/2000 | Hickey | EP | 0274873 B1 | 7/1988 |
| 6,074,670 | A | 6/2000 | Stamm | EP | 0288973 B1 | 11/1988 |
| 6,080,767 | A | 6/2000 | Klein | EP | 0311366 B1 | 4/1989 |
| 6,080,778 | A | 6/2000 | Yankner | EP | 0333268 A1 | 9/1989 |
| 6,084,082 | A | 7/2000 | Ravikumar | EP | 0337549 A1 | 10/1989 |
| 6,090,830 | A | 7/2000 | Myers | EP | 0365364 A2 | 4/1990 |
| 6,090,839 | A | 7/2000 | Adams | EP | 0369686 A1 | 5/1990 |
| 6,093,812 | A | 7/2000 | Thiruvengadam | EP | 0375527 A1 | 6/1990 |
| 6,096,883 | A | 8/2000 | Wu | EP | 0199630 B1 | 9/1990 |
| 6,099,865 | A | 8/2000 | Augello | EP | 0401705 A3 | 12/1990 |
| 6,103,705 | A | 8/2000 | Uzan | EP | 0415487 A2 | 3/1991 |
| 6,110,493 | A | 8/2000 | Guentensberger | EP | 0455042 A1 | 11/1991 |
| 6,117,429 | A | 9/2000 | Bucci | EP | 0457514 A1 | 11/1991 |
| 6,121,319 | A | 9/2000 | Somers | EP | 0461548 A3 | 12/1991 |
| 6,127,424 | A | 10/2000 | Martin | EP | 0462667 A2 | 12/1991 |
| 6,133,001 | A | 10/2000 | Homann | EP | 0475148 A1 | 3/1992 |
| 6,139,873 | A | 10/2000 | Hughes | EP | 0475755 B1 | 3/1992 |
| 6,140,354 | A | 10/2000 | Dax | EP | 0481671 A1 | 4/1992 |
| 6,143,885 | A | 11/2000 | Choi | EP | 0482498 A3 | 4/1992 |
| 6,147,090 | A | 11/2000 | DeNinno | EP | 0524595 A1 | 1/1993 |
| 6,147,109 | A | 11/2000 | Liao | EP | 0337549 B1 | 10/1995 |
| 6,147,250 | A | 11/2000 | Somers | EP | 0720599 B1 | 7/1996 |
| 6,159,997 | A | 12/2000 | Tsujita | EP | 0457514 B1 | 8/1996 |
| 6,162,805 | A | 12/2000 | Hefti | EP | 0 753 298 A1 | 1/1997 |
| 6,166,049 | A | 12/2000 | Smith et al. | EP | 0793958 A2 | 9/1997 |
| 6,174,665 | B1 | 1/2001 | Dullien | EP | 0814080 A1 | 12/1997 |
| 6,180,138 | B1 | 1/2001 | Engh | EP | 0904781 A2 | 3/1999 |
| 6,180,625 | B1 | 1/2001 | Persson | EP | 1 036 563 A1 | 9/2000 |
| 6,180,660 | B1 | 1/2001 | Whitney | EP | 1048295 A2 | 11/2000 |
| 6,191,117 | B1 | 2/2001 | Kozachuk | FR | 1103113 | 10/1955 |
| 6,191,159 | B1 | 2/2001 | Pinto | FR | 2779347 | 12/1997 |
| 6,200,998 | B1 | 3/2001 | Sahoo | GB | 861367 | 2/1961 |
| 6,207,697 | B1 | 3/2001 | Han | GB | 902658 | 8/1962 |
| 6,207,699 | B1 | 3/2001 | Rothman | GB | 1415295 | 11/1975 |
| 6,207,822 | B1 | 3/2001 | Thiruvengadam | GB | 2329334 A | 3/1999 |
| 6,214,831 | B1 | 4/2001 | Yokoo | JP | 136485 | 5/1981 |
| 6,235,706 | B1 | 5/2001 | Gould | JP | 028057 | 10/1981 |
| 6,242,605 | B1 | 6/2001 | Raveendranath | JP | 180212 | 3/1986 |
| 6,245,743 | B1 | 6/2001 | Marlowe | JP | 121479 | 12/1986 |
| 6,248,781 | B1 | 6/2001 | Jeppesen | JP | 61280295 A | 12/1986 |
| 6,251,852 | B1 | 6/2001 | Gould | JP | 219681 | 4/1987 |
| 6,262,042 | B1 | 7/2001 | Cook | JP | 63017859 A | 1/1988 |
| 6,262,047 | B1 | 7/2001 | Zhu | JP | 91068020 | 10/1991 |
| 6,262,098 | B1 | 7/2001 | Huebner | JP | 4054182 A | 2/1992 |
| 6,277,584 | B1 | 8/2001 | Chu | JP | 4266869 A | 9/1992 |
| 6,316,029 | B1 | 11/2001 | Jain | JP | 4356195 A | 12/1992 |
| RE37,721 | E | 5/2002 | Rosenblum | JP | 4356495 | 12/1992 |
| 2001/0028895 | A1 | 10/2001 | Bisgaler | JP | 5058993 A | 3/1993 |
| 2002/0006919 | A1 | 1/2002 | Thosar | JP | 5194209 A | 8/1993 |
| 2002/0039774 | A1 | 4/2002 | Kramer et al. | JP | 5239020 A | 9/1993 |
| 2002/0128252 | A1 | 9/2002 | Glombik et al. | JP | 94047573 | 6/1994 |
| 2002/0128253 | A1 | 9/2002 | Glombik et al. | JP | 95051558 B2 | 6/1995 |
| 2002/0132855 | A1 | 9/2002 | Nelson et al. | WO | WO 82/01649 | 5/1982 |
| 2002/0137689 | A1 | 9/2002 | Glombik et al. | WO | WO 87/04429 | 7/1987 |
| 2002/0169134 | A1* | 11/2002 | Davis ............... 514/23 | WO | WO 88/04656 | 6/1988 |
| 2002/0192203 | A1* | 12/2002 | Cho et al. ............ 424/94.1 | WO | WO 88/05296 | 7/1988 |
| 2003/0013729 | A1* | 1/2003 | Iqbal et al. ............ 514/269 | WO | WO 91/03249 | 3/1991 |
| 2003/0119428 | A1* | 6/2003 | Davis et al. ............ 451/59 | WO | WO 92/13837 | 8/1992 |
| 2003/0119757 | A1* | 6/2003 | Davis ............... 514/25 | WO | WO 93/02048 | 2/1993 |
| 2003/0153541 | A1 | 8/2003 | Dudley et al. | WO | WO 93/07167 | 4/1993 |
| | | | | WO | WO 93/11150 | 6/1993 |
| | | FOREIGN PATENT DOCUMENTS | | WO | WO 94/00480 | 1/1994 |
| | | | | WO | WO 94/14433 | 7/1994 |
| CA | | 2253769 | 11/1999 | WO | WO 94/17038 | 8/1994 |
| DE | | 2046823 A | 3/1972 | WO | WO 94/20535 | 9/1994 |

| | | | | | | |
|---|---|---|---|---|---|---|
| WO | WO 94/26738 | 11/1994 | | WO | WO 00/38723 | 7/2000 |
| WO | WO 95/04533 | 2/1995 | | WO | WO 00/38724 | 7/2000 |
| WO | WO 95/06470 | 3/1995 | | WO | WO 00/38725 | 7/2000 |
| WO | WO 95/08532 | 3/1995 | | WO | WO 00/38726 | 7/2000 |
| WO | WO 95/18143 | 7/1995 | | WO | WO 00/38727 | 7/2000 |
| WO | WO 95/26334 | 10/1995 | | WO | WO 00/38728 | 7/2000 |
| WO | WO 95/28919 | 11/1995 | | WO | WO 00/38729 | 7/2000 |
| WO | WO 95/35277 | 12/1995 | | WO | WO 00/40247 | 7/2000 |
| WO | WO 96/00288 | 1/1996 | | WO | WO 00/45817 | 8/2000 |
| WO | WO 96/09827 | 4/1996 | | WO | WO 00/50392 | 8/2000 |
| WO | WO 96/16037 | 5/1996 | | WO | WO 00/53149 | 9/2000 |
| WO | WO 96/19450 | 6/1996 | | WO | WO 00/53173 | 9/2000 |
| WO | WO 96/19987 | 7/1996 | | WO | WO 00/53563 | 9/2000 |
| WO | WO 96/40255 | 12/1996 | | WO | WO 00/56403 | 9/2000 |
| WO | WO 97/16455 | 5/1997 | | WO | WO 00/57859 | 10/2000 |
| WO | WO 97/18304 | 5/1997 | | WO | WO 00/57918 | 10/2000 |
| WO | WO 97/21676 | 6/1997 | | WO | WO 00/60107 | 10/2000 |
| WO | WO 97/25042 | 7/1997 | | WO | WO 00/63153 | 10/2000 |
| WO | WO 97/28149 | 8/1997 | | WO | WO 00/63161 | 10/2000 |
| WO | WO 97/31907 | 9/1997 | | WO | WO 00/63190 | 10/2000 |
| WO | WO 97/35576 | 10/1997 | | WO | WO 00/63196 | 10/2000 |
| WO | WO 97/41098 | 11/1997 | | WO | WO 00/63209 | 10/2000 |
| WO | WO 97/46238 | 12/1997 | | WO | WO 00/63703 | 10/2000 |
| WO | WO 98/01100 | 1/1998 | | WO | WO 00/69412 | 11/2000 |
| WO | WO 98/05331 | 2/1998 | | WO | WO 00/69445 | 11/2000 |
| WO | WO 98/14179 | 4/1998 | | WO | WO 00/72825 | 12/2000 |
| WO | WO 98/31360 | 7/1998 | | WO | WO 00/72829 | 12/2000 |
| WO | WO 98/31361 | 7/1998 | | WO | WO 00/75103 | 12/2000 |
| WO | WO 98/31366 | 7/1998 | | WO | WO 00/76482 | 12/2000 |
| WO | WO 98/43081 | 10/1998 | | WO | WO 00/76488 | 12/2000 |
| WO | WO 98/46215 | 10/1998 | | WO | WO 00/78312 | 12/2000 |
| WO | WO 98/47518 | 10/1998 | | WO | WO 00/78313 | 12/2000 |
| WO | WO 98/57652 | 12/1998 | | WO | WO 01/00579 | 1/2001 |
| WO | WO 99/06035 | 2/1999 | | WO | WO 01/00603 | 1/2001 |
| WO | WO 99/06046 | 2/1999 | | WO | WO 01/08686 | 2/2001 |
| WO | WO 99/08501 | 2/1999 | | WO | WO 01/12176 | 2/2001 |
| WO | WO 99/09967 | 3/1999 | | WO | WO 01/12187 | 2/2001 |
| WO | WO 99/11260 | 3/1999 | | WO | WO 01/12612 | 2/2001 |
| WO | WO 99/12534 | 3/1999 | | WO | WO 01/14349 | 3/2001 |
| WO | WO 99/04815 | 4/1999 | | WO | WO 01/14350 | 3/2001 |
| WO | WO 99/15159 | 4/1999 | | WO | WO 01/14351 | 3/2001 |
| WO | WO 99/15520 | 4/1999 | | WO | WO 01/15744 | 3/2001 |
| WO | WO 99/18072 | 4/1999 | | WO | WO 01/16120 | 3/2001 |
| WO | WO 99/20275 | 4/1999 | | WO | WO 01/17994 | 3/2001 |
| WO | WO 99/20614 | 4/1999 | | WO | WO 01/18210 | 3/2001 |
| WO | WO 99/22728 | 5/1999 | | WO | WO 01/21181 | 3/2001 |
| WO | WO 99/29300 | 6/1999 | | WO | WO 01/21259 | 3/2001 |
| WO | WO 99/38498 | 8/1999 | | WO | WO 01/21578 | 3/2001 |
| WO | WO 99/38845 | 8/1999 | | WO | WO 01/21647 | 3/2001 |
| WO | WO 99/38850 | 8/1999 | | WO | WO 01/22962 | 4/2001 |
| WO | WO 99/46232 | 9/1999 | | WO | WO 01/25225 | 4/2001 |
| WO | WO 99/47123 | 9/1999 | | WO | WO 01/25226 | 4/2001 |
| WO | WO 99/48488 | 9/1999 | | WO | WO 01/30343 | 5/2001 |
| WO | WO 99/66929 | 12/1999 | | WO | WO 01/32161 | 5/2001 |
| WO | WO 99/66930 | 12/1999 | | WO | WO 01/34148 | 5/2001 |
| WO | WO 00/04011 | 1/2000 | | WO | WO 01/35970 | 5/2001 |
| WO | WO 00/07617 | 2/2000 | | WO | WO 01/40192 | 6/2001 |
| WO | WO 00/16749 | 3/2000 | | WO | WO 01/45676 | 6/2001 |
| WO | WO 00/18395 | 4/2000 | | WO | WO 01/49267 | 7/2001 |
| WO | WO 00/20623 | 4/2000 | | WO | WO 01/60807 | 8/2001 |
| WO | WO 00/23415 | 4/2000 | | WO | WO 01/64221 | 9/2001 |
| WO | WO 00/23416 | 4/2000 | | WO | WO 01/76632 | 10/2001 |
| WO | WO 00/23425 | 4/2000 | | WO | WO 01/96347 | 12/2001 |
| WO | WO 00/23445 | 4/2000 | | WO | WO 02/08188 | 1/2002 |
| WO | WO 00/23451 | 4/2000 | | WO | WO 02/26729 | 4/2002 |
| WO | WO 00/28981 | 5/2000 | | WO | WO 02/50027 | 6/2002 |
| WO | WO 00/31548 | 6/2000 | | WO | WO 02/50060 | 6/2002 |
| WO | WO 00/32189 | 6/2000 | | WO | WO 02/50068 | 6/2002 |
| WO | WO 00/34240 | 6/2000 | | WO | WO 02/50090 | 6/2002 |
| WO | WO 00/37057 | 6/2000 | | WO | WO 02/058685 | 8/2002 |
| WO | WO 00/37078 | 6/2000 | | WO | WO 02/058696 | 8/2002 |
| WO | WO 00/38721 | 7/2000 | | WO | WO 02/058731 | 8/2002 |
| WO | WO 00/38722 | 7/2000 | | WO | WO 02/058732 | 8/2002 |

| | | |
|---|---|---|
| WO | WO 02/058733 | 8/2002 |
| WO | WO 02/058734 | 8/2002 |
| WO | WO 02/064094 | 8/2002 |
| WO | WO 02/064130 | 8/2002 |
| WO | WO 02/064549 | 8/2002 |
| WO | WO 02/064664 | 8/2002 |
| WO | WO 02/072104 | 9/2002 |
| WO | WO 02/081454 | 10/2002 |
| WO | WO 03/018024 | 3/2003 |
| WO | WO 03/018059 | 3/2003 |
| WO | WO 03/039542 | 5/2003 |
| WO | WO 03/074101 | 9/2003 |
| WO | WO 03/088962 | 10/2003 |

OTHER PUBLICATIONS

U.S. Appl. No. 10/057,646, filed Jan. 25, 2002, Harry R. Davis et al.
U.S. Appl. No. 10/057,629, filed Jan. 25, 2002, Harry R. Davis.
U.S. Appl. No. 10/154,106, filed May 22, 2002, Harry R. Davis et al.
U.S. Appl. No. 10/057,323, filed Jan. 25, 2002, Harry R. Davis et al.
U.S. Appl. No. 10/136,968, filed May 1, 2002, Wing-Kee Philip Cho et al.
U.S. Appl. No. 10/057,339, filed Jan. 25, 2002, Teddy Kosoglou et al.
U.S. Appl. No. 10/247,032, filed Jan. 25, 2002, Harry R. Davis.
U.S. Appl. No. 10/056,680, filed Jan. 25, 2002, Teddy Kosoglou et al.
U.S. Appl. No. 10/247,099, filed Sep. 19, 2002, Harry R. Davis et al.
U.S. Appl. No. 10/247,085, filed Sep. 19, 2002, John T. Strony.
U.S. Appl. No. 10/246,996, filed Sep. 19, 2002, Alexandre P. Lebeaut et al.
U.S. Appl. No. 10/247,397, filed Sep. 19, 2002, Harry R. Davis et al.
U.S. Appl. No. 10/166,942, filed Jun. 11, 2002, Anima Ghosal et al.
Vaccaro, W.D. et al , "Sugar-substituted 2-azetidinone cholesterol absorption inhibitors: enhanced potency by modification of the sugar" *Bioorganic & Medicinal Chemistry Ltrs.*, Oxford, G.B., 8:313-318 (1998).
Vaccaro, W.D. et. al., "Carboxy-substituted 2-azetidinones as cholesterol absorption inhibitors", *Bioganic & Medicinal Chem. Ltrs.* Oxford, G.B. 8:319-322 (1998).
H. Davis et al., "Ezetimibe, a Potent Cholesterol Absorption Inhibitor, Inhibits the Developmentof Aterosclerosis in Apo E Knockout Mice", *Arterioscler, Thromb. Vasc. Biol* 21:2032-2038, (Dec. 2001).
Simova, E., "Aldol-type addition of hydrocinnamic acid esters to benzylideneaniline", *Chemical Abstracts* No. 15, 86 (Apr. 11, 1997).
Otto et al., Stereochemistry of dehydration and halogenation fo αR* and αS* isomeric 3-(α-hydroxybenzyl)-1,4 diphenyl=2 azetidinones, *Chemical Abstracts* No. 19, 99 (Nov. 7, 1983).
T. Durst et al, "Metallation of N-Substituted β-Lactams. A Method of the Introduction of 3-substituents into β-Lactams" *Canadian Journal of Chemistry*, 50:3196-3201 (1971).
Nobuki, O. et al., "Stereoselective syntheses of b-lactam derivatives by ultrasound promoted Reformatskii reaction" *Chemical Abstracts* No. 106, 17 (Apr. 27, 1987).
M. Hoekman, et al., "Synthesis of Homologues of 4,5-Dihydroxy- and 4-Hydroxy-5-oxohexanoic Acid γ-Lactones", *J. Agric. Food Chem.*, 30:920-924 (1982).
H. Otto et al. "Darstellung and Stereochemie von 3-(α-Hydroxybenzyl)-1,4-diphenyl-2-azetidononen", *Liebigs Ann. Chem.* 1152-1161 (1983).
G. George et al. "3-(1'-Hydroxyethyl)-2-Azetidinones From 3-Hydroxybutyrates and N-Arylaldimines" *Tetrahedron Letters*, 26:3903-3906 (1985).
Hart et al. "An Enantioselective Approach to Carbapenem Antibodies: Formal Synthesis of (+)-Thienamycin", 26 *Tetrahedron Letters*, 45:5493-5496 (1985).

Panfil, I. et al. "Synthesis of β-Lactams from α, β-Unsaturated Sugar δ-Lactones" 24 *Heterocycles* 6:1609-1617 (1986).
D. Roger Illingworth, "An Overview of Lipid-Lower Drugs" *Drugs* 36:63-71 (1988).
Joseph L. Witztum, M.D., "Current Approaches to Drug Therapy for the Hyercholesterolemic Patient" *Circulation* 80:1101-1114 (1989).
B. Ram et al. "Potential Hypolipidemic agents:Part V", 29B Indian J. Chem. 1134-37 (1990).
Schnitzer-Polokoff, R. et al., "Effects of Acyl-CoA: Choleseraol O-Acyltransferase Inhibition on Cholesterol Absorption and Plasma Lipoprotein Composition in Hamsters" Comp. Biochem. Physiol. 99A:665-670 (1991).
Horie, M. et al, "Hypolipidemic effects of NB-598 in dogs" *Atherosclerosis* 88:183-192 (1991).
Baxter, A., "Squalestatin 1, a Potent Inhibitor of Squalene Synthase, Which Lowers Serum Cholesterol in Vivo", *The Journal of Biological Chemistry* 267:11705-11708 (1992).
Summary Factfile, "Anti-Antherosclerotic Agents" *Current Drugs Ltd.* (1992).
Harwood H. James, "Pharmacologic consequences of cholesterol absorption inhibition: alteration in cholesterol metabolism and reduction in plasma cholesterol concentration induced by the synthetic saponin β-tigogenin cellobioside (CP-88818; tiqueside) 1" *Journal of Lipid Research* 34:377-395 (1993).
Salisbury, B. et al., "Hypocholesterolemic activity of a novel inhibitor of cholesterol absorption, SCH 48461" *Atherosclerosis* 115:45-63 (1995).
Clader, J. W. et al., "Substituted (1,2-Diarylethyl)amide-Acyl-CoA;Cholesterol Acyltransferase Inhibitors: Effect of Polar Groups in Vitro and in Viro Activity" *Journal of Medicinal Chemistry* 38:1600-1607 (1995).
Sybertz, E., "Sch 48461, a novel inhibitor of cholesterol absorption" Atherosclerosis pp. 311-315 (1995).
Vaccaro, W, et al, "2-Azetidinone Cholesterol Absorption Inhibitors; Increased Potency by Substitution of the C-4 Phenyl Ring", *Bioorg. & Med. Chem.* 6:1429-1437 (1998).
G. Wu et al, A Novel One-Step Diastereo-and enantioselective formation of trans-azetidinones and its application to the total synthesis of cholesterol absorption inhibitors A.C.S. (Apr. 21, 1999).
B. Staels, "New Roles for PPARS in Cholesterol Homeostasis", *Trends in Pharmacological Sciences*, 22:9 p. 444 (Sep. 2001).
Abbott et al, "Tricor® Capsules, Micronized", *Physicians Desk Reference*, Jan. 8, 2001.
M. Feher et al., 1991, Lipids and Lipid Disorders, p. 1-87 (1991).
M. Ricote et al., "New Roles for PPARs in Cholesterol Homeostakis", *Trends in Pharmacological Science*, vol. 22, No. 9 441-443 (2001).
C. Dujovne et al, "Reduction of LDL Cholesteral in Patients with Primary Hypercholesterolemia by SCH 48461: Results of a mutlicenter Dose-Ranging Study", *J. Clin,. Pharm*. 41:1 70-78 (Jan. 2001).
W. Oppolzer et al., "Asymmetric Diels—Alder Reactions, Facile Preparation and Structure of Sulfonamido—Isobornyl Acrylates", *Tetrahedron Letters* No. 51, 25:5885-5888 (1984).
M. Davidson et al., "Colesevelam Hydischloride: a non-absorbed, polymeric cholesterol lowing agent", *Expert Opinion Investigating Drugs*, 11:2663-71, (Nov. 2000).
M. Davidson et al., "Colesevelam hydrochloride (cholestagel): a new, potent bileacid sequestrant associated with a low incidence of gastrointestinal effects", 159 *Arch. Intern. Med.* 16 1893-900 (Sep. 1999).
I. Wester, "Cholesterol—Lowering effect of plant sterols", *Euro. J.Lipid, Sci. Tech.* 37-44 (2000).
A. Andersson et al., "Cholesterol—lowering effects of a stanol ester-containing low fat margarine used in conjunction with a strict lipid-lowing diet", *1 European Heart. J. Supplements* S80-S90 (1999).
H. Gylling et al, Reduction of Serum Cholesterol in Postmenopausal Women with Previous Myocardial Infarction and Cholesterol Malabsorption induced by Dietary Sitostarol Ester Margarine, 96 *Circulation12* 4226-4231 (Dec. 16, 1997).

T. Miettinen et al, "Reduction of Serum Cholesterol with Sitostanol-Ester Margarine in a Mildly Hypercholesterolemic Population", *New England Journal of Med.* 333 1308-1312 (Nov. 16, 1995).

T. Bocan et al., "The ACAT Inhibitor Avasimibe Reduces Macrophages and Matrix Metalloproteinase Expression in Atherosclerotic Lesions of Hypercholesterolemic Rabbits", *Arterioscler Thromb Vasc. Biol.* 70-79 (Jan. 2000).

M. Van Heek et al., "In Vivo Metabolism—Based Discovery of a Potent Cholesterol Absorption Inhibitor, SCH 58235, in the Rat and Rhesus Monkey through the indentification of the active metabolites of SCH48461," *283 J. Pharma and Experimental Therapeutics 1* 157-163 (1997).

H. Davis et al., "The Cholesterol Absorption Inhibitor Ezetimible Inhibits the Development of Atherosclerosis in apo E knockout (-/-) mice fed low fat and western diets," *151 Atherosclerosis 1*:133 (Jul. 2000).

L. Nguyen et al., "Unexpected Failure of Bile Acid Malabsorption to Stimulate Cholesterol Synthesis in Sitosterolemia with Xanthomatosis", *10 Atherosclerosis 2*, 289-297 (1990).

L. Nguyen et al., "Regulation of Cholesterol Biosynthesisin Sitosterolemia: effects of lovastatin, Cholestyramine, and dietary sterol restriction," *32 J.Lipid Res.* 1941-1948 (1991).

M. Cobb et al., "Sitosterolemia: Opposing Effects of cholestyramine and Lovastatin on Plasma Sterol Levels in a Homozygous Girl and Her Heterozygous Father," *45 Metabolism 6* 673-679 (Jun. 1996).

M. Huettinger et al., "Hypolipidemic Activity of HOE-402 is mediated by Stimulation of the LDL Receptor Pathway", *13 Arteriosclerosis and Thrombosis 7* 1005-1012 (Jul. 1993).

J. Best et al., "Diabetic Dyslipidaemia", *59 Drugs 5* 1101-1111 (May 2000).

P. Chong, et al, "Current, New and Future Treatment in Dyslipidaemia and Atherosclerosis", *60 Drugs 1* 55-93 (Jul. 2000).

M. Brown et al, "A Receptor—Mediated Pathway for Cholesterol Homeostasis", *232 Science* 34-47 (Apr. 4, 1986).

L. Lipka et al., "Reduction of LDL-Cholesterol and Elevation of HDL-Cholesterol in Subjects with Primary Hypercholesterolemia by SCH 58235: Pooled Analysis of Two Phase II Studies", *JACC* 257A (Feb. 2000).

Medical Economics, Co., Inc., *Physician's Desk Reference*, 207-208, 2054 (55th Ed. 2001).

K. Fassbender et al., "Simvastatin Strongly Reduces Levels of Alzheimer's Disease β-Amyloid Peptides Aβ 42 and Aβ40 in vitro and in vivo", *PNAs Early Edition*, www.phas.org/cgi/doi/10,1073/phas.081620098 (2001).

Andrx Announces Results of Alzheimer's Disease Clinical Study, *Andrx Corporate Release* (Apr. 11, 2001).

Andrx (ADRX): Pos Phase II Results Using Avicor in Alzheimer's: Str Buy; $130,*US Bancorp Piper*, Apr. 12, 2001.

Statins May Protect Against Alzheimer's Disease; much research needed, *Geriatrics* Feb. 2001.

Dementia and Statins, *The Lancet* Mar. 17, 2001.

Research & Development: Andrx Says Cholesterol Drug May Treat Alzheimers, *Reuters* Apr. 11, 2001.

Cholesterol Drugs Ease Alzheimer's Damage; www.usatoday.com Apr. 10, 2001.

Lovastation XL of Use in Alzheimer's? News Edge (May 2, 2001).

L. Refolo et al, Hypercholesterolemia Accelerates the Alzheimer's Amyloid Pathology in a Transgenic Morse Model, *Neurobiology of Disease* 321-331 (2000).

D. Kang et al., "Modulation of Amyloid β-protein Clearance and Alheimer's Disease Susceptibility by the LDL Receptor—Related Protein Pathway", *Journal of Clinical Investigation* 106:9, 1159-1166 (Nov. 2000).

Y.A. Kesaniewmi, "Intestinal Cholesterol Absorption Efficiency in Man is Related to Apoprotein E Phenotype", *J. Clin. Invest.* 80(2) 578-81 (Aug. 1987).

J. Busciglio et al., "Generation of β-amyloid in the secretary pathway in neuronal and nonneuronal cells", *90 Proc. Nat'l Acad. Sci, USA*, 2092-2096 Neurobiology (Mar. 1993).

L. Farrer et al., "Assessment of Genetic Risk for Alzheimer's Disease Among first Degree Relatives", *Annals of Neurology* 25:5, 485-493 (May 1989).

A. Goate et al., "Segregation of a Missense Mutation in the Amyloid Precursor Protein Gene with Familial Alzheimer's Disease", *349 Nature* No. 6311, 704-706 (Feb. 21, 1991).

D. Mann et al., "The Pattern of Acquisition of Plaques and Tangle in the Brains of Patients Under 50 years of Age with Down's Syndrome", *89 J. Neuro. Sci.*, 169-179 (Feb. 1989).

G. McKhann et al., "Clinical Diagnosis of Alzheimer's Disease", *34 Neurology* No. 7, 939-944 (Jul. 1984).

D. Selokoe, "Alzheimer's Disease: Genotypes, Pheontype and Treatments", *275 Science*, 630-631 (Jan. 31, 1997).

C. Van Duijn, et al., "Familial Aggregation of Alzheimer's Disease and Related Disorders: A collaborative Re-Analysis of Case-Control Studies", *20 Int'l J. Epidemiology* No. 2 (Suppl. 2), 513-520 (1991).

T Nagahara et al., "Dibasic (Amidcinoaryl) Propanoic Acid Derivatives as Novel Blood Coagulation Factor Xa Inhibitors", *J. Med. Chem* 37:1200-1207 (1994).

Mellott et al., "Acceleration of Recombinant Tissue-Type Plasminogen Activator Induced Reperfusion and Prevention of Reocculsion by Recombinant Antistasin, a selective factor Xa Inhibitor, in a Canine Model of Femoral Arterial Thrombosis", *Circulation Research*, 70:1152-1160 (1992).

Sitko et al., "Conjunctive Enhancement of Enzymatic Thrombolysis and Prevention of Thrombotic Reocclusion With the Selective Factor Xa Inhibitor, Tick Anticoagulant Peptide", *Circulation*, 85:805-815 (1992).

Seymour et al., 1994, *Biochemistry*, 33:3949-3959.

Markwardt, 1994, *Thrombosis and Hemostasis*, 72:477-479.

Mendall et al., "C-Reactive Protein and its relation to cardiovascular risk factor: A population based cross sectional study", *BMJ*; 312:1061-1065 (Apr. 27, 1996).

Ridker P. et al., "Prospective Studies of C-Reactive Protein as a risk factor for cardiovascular disease", *46 J. Investig. Med.*; 8:391-395 (1998).

L. Gruberb, 2000, "Inflammatory Markers in Acute Coronary Syndromes: C-reative protein (CRP) and Chlamydia", *American Heart Association Scientific Sessions*.

Waters, D. et al., "A Controlled Clinical Trial to Assess the Effect of a Calcium Channel Blocker on the Progression of Coronary Atherosclerosis", *Circulation*; 82:1940-1953 (1990).

Fleckenstein, 1985, *Cir. Res.* vol. 52 (Suppl. 1) 3-16.

Fleckenstein, 1983, "Experimental Facts and Therapeutic Prospects", John Wiley, New York, pp. 286-313.

McCall, D., 1985, *Curr. Pract. Cardiol.* vol. 10, 1-11.

Remington 1995, The Science and Practice of Pharmacy, (19th Ed. 1995) p. 963.

M. Chistie et al., "Early—Onset Amyloid Deposition and Cognitive Deficits in Transgenic Mice Expressing a Double Mutant Form of Amyloid Precursor Protein 695", *276 J. Biol. Chem.* No. 24; 21562-70 (Jun. 15, 2001).

C. Janus et al., "Aβ Peptide Immunization Reduces Behavioral impairment and Plaques in a Model of Alzheimer's Disease", *408 Nature 21/28*; 979-982 (Dec. 2000).

Manual of Laboratory Operations, Lipid Research Clinics Program Report, Washington, D.C., *U.S. Dept. of Health, Education and Welfare Publication*; 1:75-628 (1974).

Steiner, PM et al., Standardization of Micromethods for Plasma Cholesterol, Triglyceride and HDL-Cholesterol with the Lipid Clinic's Methodology [abstract], *J. Clin. Chem. Clin. Bichem*; 19:850 (1981).

Steele WG, et al., Enzymatic Determinations of Cholesterol in High Density Lipoprotein Fractions Prepared by Precipitation Technique,22 *Clin. Chem.*; 1:98-101 (1976).

Salen et al., "Increased Sitosterol Absorption, Decreased Removal and Expanded Body Pools Compensate for Reduced Choelsterol Syntheses in Sitosterolemia with Xanthomatosis", *J. Lipd Res.*,; 30:1319-1330 (1989).

Lutjohann et al., "Sterol Absorption and Sterol Balance in Phytosterolemia Evaluated by Deuterium-Labeled Sterols: Effect of Sitostanol Treatment", *J. Lipid Res.*; 36:8; 1763-1773 (1995).

Zhang et al., "Calpain Inhibitor I Increases B- Amyloid Peptide by Inhibiting the Degradation of the Substrate of γ- Secretase" 274 *J. Biol, Chem.*, 13:8966-8972 (1999).

Zhang et al., "Biochemical Characterization of the γ-Secretase Activity that Produces B-Amyloid Peptides", Biochemistry 40:5049-5055 (2001).

Ida et al., "Analysis of Heterogeneous BA4 Peptides in Human Cerebrospinal Fluid and Blood by a Newly Developed Sensitive Western Blot Assay", 271 *J. Biol, Chem.*; 37:22908-22914 (1996).

Lichtlen, P.R. et al., 1990, *Lancet*; 335:1109-1113.

Bays et al., "Effectiveness and Tolerability of Ezetimibe in Patients with Primary Hypercholesterolemia: Pooled Analysis of Two Phase II Studies", *Clinical Therapeutics*, 23:1209-1230 (2001).

E. Leitersdorf et al., "Cholesterol absorption inhibition: filling an unmet need it lipid-lowering management", *European Heart Journal Supplement*, 3:E17-E23 (Jun. 2001).

Bauer et al., "Ezetimibe Does not Affect the Pharmacokinetics or Pharmacodynamics of Warfarin", *Clinical Pharmacology and Therapeutics*, 69:2 p. 5 (Mar. 6-10, 2001).

Keung et al., Ezetimibe Does Not Affect the Pharmacokinetics of oral Contraceptives, *Clinical Pharmacology and Therapeutics*, 69:2 p. 55 (Mar. 6-10, 2001).

Kosoglou et al., "Pharmacodynamic interaction between fenofibrate and the Cholesterol Absorption Inhibitor Ezetimibe", *Workshops Lipid Lowering Drugs 72nd EAS Congress*, p. 38 (May 21-23, 2001).

T. Kosoglou et al., "Coadministration of Ezetimibe and Fenofibrate Leads to Favorable Effects On Apo CII and LDL Subfractions", *Posters 11. Lipid Lowering Drugs/Novel, 72nd EAS Congress*, p. 89 (May 21-23, 2001).

L. Reyderman et al., "Assessment of a Multiple-Dose Drug Interaction Between Ezetimibe and Gemfibrozil", Presented at XIV Int'l Symp. on Drugs Affecting Lipid Metabolism (DALM) N.Y. (Sep. 9-12, 2001).

P. Statkevich et al., "Ezetimibe Does Not Affect the Pharmacokinetics and Pharmacodynamics of Glipizide",*Clinical Pharmacology & Therapeutics*, 69:67 (Mar. 6-10, 2001).

Knopp et al, "Effect of Ezetimibe on Serum Concentrations of Lipid-Soluble Vitamins", *Posters 11. Lipid Lowering Drug/Novel 72hd EAS Congress*, p. 90 (May 21-23, 2001).

Kosoglou et al., "Pharmacodynamic Interaction Between Fenofibrate and the Cholesterol Absorption Inhibitor Ezetimibe", *Workshops Lipid Lowering Drugs, 72nd EAS Congress*, p. 38 (Mar. 6-10, 2001).

Bays et al., "Low-Density Lipoprotein Cholesterol Reduction By SCH 58235 (Ezetimibe), A Novel Inhibitor of Intestinal Cholesterol Absorption, in 243 Hypercholesterolemic Subjects: Results of a Dose-Response Study", *XII International Symposium on Atherosclerosis*, Stockholm, Sweden (Jun. 25-29, 2000).

Castaner et al, "Ezetimibe—Hypolipidemic Cholesterol Absorption Inhibitor", *Drugs of the Future*, 25(7):679-685 (2000).

Lipka et al., "Reduction of LDL-Cholesterol and Elevation of HDL-Cholesterol in Subjects with Primary Hypercholesterolemia by Ezetimibe (SCH 58235): Pooled Analysis of Two Phase II Studies", *American College of Cardiology Annual Meeting*, Anaheim, CA (Mar. 12-15, 2000).

Van Heek et al., "Comparison of the activity and disposition of the novel cholesterol absorption inhibitor , SCH58235, and its glucuronide, SCH60663", *British Journal of Pharmacology*, 129:1748-1754 (2000).

Van Heek et al., 2000, "The potent cholesterol absorption inhibitor, ezetimibe, is glucuronidated in the intestine, localizes to the intestine, and circulates enterohepatically", *XII International Symposium of Atherosclerosis*, Stockholm Sweden (Jun. 25-29, 2000).

Iannucci et al., "Metabolism of SCH 58235 in the Human, Rat and Dog", *47th ASMS Conference on Mass Spectrometry and Allied Topics*, Dallas, TX (Jun. 13-17, 1999).

Reiss et al., "An Enzymatic Synthesis of Glucuronides of Azetidinone-based Cholesterol Absorption Inhibitors", *Bioorganic & Medicinal Chemistry*, 7:2199-2202 (1999).

Rosenblum et al., "Discovery of 1-(4-Flurophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem.* 41:973-980 (1998).

Vaccaro et al., "Sugar-Substituted 2-Azetidinone Cholesterol Absorption Inhibitors: Enhanced Potency by Modification of the Sugar", *Bioorganic & Medicinal Chemistry Letters*, 8:313-318 (1998).

Zaks et al., "Enzymatic Glucuronidation of a Novel Cholesterol Absorption Inhibitor, SCH 58235", *Applied Biochemistry and Biotechnology*, 73:205-214 (1998).

W. Insull et al., Postmenopausal Hypercholesterolemic Women Derive Additive Benefit from Raloxifene and Simvastatin on Lipid Parameters , *World Heart Federation 6th International Symposium on Global Risk of Coronary Heart Disease and Stroke—Abstract Book*, p. 35 (Jun. 12-15, 2002).

L. Simons et al., 2002, "Ezetimibe added to on-going statin therapy for treatment of primary hypercholesterolemia: Efficacy and safety in patients with Type 2 diabetes mellitus", presented at the 38th Annual Meeting of the EASD, Sep. 1-5, 2002.

C. Allain et al, 1974, "Enzymatic Determination of Total Serum Cholesterol", *Clinical Chemical*, 20:470-475.

R. Mayrhofer et al., 1980, "Simple-Preparation of 3-Benzylidene-2-azetilidinones", *Synthesis*, 247-248.

Burrier, R.E. et al., 1994, "Demonstration of a Direct Effect on Hepatic Acyl CoA:Cholesterol Acyl Transferase (ACAT) Activity By An Orally Administered Enzyme Inhibitor in the Hamster", *Biochemical Pharmacology* 47:1545-1551.

Burrier, R.E. et al., 1994, "The Effect of Acyl CoACholesterol Acyltransferase Inhibitor on the Uptake, Esterification and Secretion of Cholesterol by the Hamster Small Intestine", *The Journal of Pharmacology and Experimental Therapeutics* 272:156-163.

E.F. Binder et al., "Effects of Hormone Replacement Therapy on Serum Lipids in Elderly Women. A Randomized, Placebo-Controlled Trial", *134 Ann. Intern. Med.* 9:754-760 (May 1, 2001).

MR Haymart et al., "Optimal Management of Dyslipidemia in Women and Men", 2 *J. Gend. Specif. Med.* 6:37-42 (Nov.-Dec. 1997).

"Framingham Heart Study Analysis Reveals Some Primary Prevention Subgroups Are Being Overlooked", *Heartwire* (Apr. 12, 2001).

Detection Evaluation, and Treatment of High Blood Cholesterol in Adults (Adult Treatment Panel III), "Third Report of the National Cholesterol Education Program (NCEP)", *NIH Publication* No. 01-3670 (May 2001).

Van Heek et al., "Ezetimibe, A Potent Cholesterol Absorption Inhibitor, Normalizes Combined Dyslipidemia in Obese Hyperinsulinemic Hamsters", 50 *Diabetes* 1330-1335 (Jun. 2001).

"Additional Statins Show Anti-Inflammatory Effect", 103 *Circulation* 1933-35 (Apr. 17, 2001).

H. Hauser, et al, "Identification of a Receptor Mediating Absorption of Dietary Cholesterol in the Intestine", *Biochemistry* 37:17843-17850, 1998.

G. Salen, et al., "Sitosterolemia", *Journal of Lipid Research* 33:945-955, 1992.

Stedman's Medical Dictionary, 27th Edition, p. 1381.

P. F. Belamarich et al., "Response to Diet and Cholestyramine in a Patient with Sitosterolemia", *Pediatrics*, 977-981, (Dec. 1990).

G. Salen et al., "Lethal Atherosclerosis Associated With Abnormal Plasma and Tissue Sterol Composition in Sitosterolemia With Xanthomatosis", *Journal of Lipid Research*, 1126-1133, (Sep. 1985).

G.R. Thompson et al., Novel Lipid-Regulating Drugs, Exp. Opin. Invest. Drugs, 9(11):2619-2628, 2000.

Thompson, G.R. et al., "Novel lipid-regulating drugs" *Expert Opinion on Investigational Drugs* 9(11):2619-2628 (2000), XP008011782 abstract; figure 8.

Kosoglou, T. et al., "Coadministration of ezetimibe and fenofibrate leads to favorable effects on Apo CII and LDL subfractions" *Atherosclerosis* 2:89 (2001), XP1132089 abstract.

Baker et al. "Treatment of homozygous familial hypercholesterolemia with probucol" *South African Medical Journal* 62(1):7-11(1982).

Milanese et al. "The prevalence diagnosis and therapy of xanthomas and hypercholesterolemia" *Chronica Dermatologica* 21(4):455-461(1990).

Luis Gruberg, MD, Inflammatory Markers in Acute Coronary Syndromes: C-reactive Protein (CRP) and Chlamydia, American Heart Association Scientific Sessions 2000.

Stuart B. Rosenblum et al., Discovery of 1-(4-Fluorophenyl)-(3R)-[3-(fluorophenyl)-(3S)-hydroxypropyl]-(4S)-(4-hydroxyphenyl)-2-azetidinone (SCH 58235): A Designed, Potent, Orally Active Inhibitor of Cholesterol Absorption, *J. Med. Chem.* 41:973-980 (1998).

Gilbert R. Thompson et al., Novel lipid-regulating drugs, *Exp. Opin. Invest. Drugs* 9(11):2619-2628 (2000).

T. Kosoglou et al., Coadministration of Ezetimibe and Fenofibrate Leads to Favorable Effects on Apo CIII and LDL Subfractions, *Atherosclerosis* 2:89 (2001).

Harry R. Davis et al., The Synergistic Hypocholesterolemic Activity of the Potent Cholesterol Absorption Inhibitor, Ezetimibe, in Combination With 3-Hydroxy-3-Methylglutaryl Coenzyme A Reductase Inhibitors in Dogs, *Metabolism* 50 (10):1234-1241 (2001).

Study Showed Ezetimibe Significantly Reduced Levels of LDL Cholesterol or "Bad" Cholesterol in Patients, Schering-Plough Press Release.

T. Kosoglou et al., Pharmacodynamic Interaction Between Fenofibrate and the Cholesterol Absorption Inhibitor Ezetimibe, *Atherosclerosis* (2):38 (2001).

Remington's Pharmaceutical Sciences, 18th ed. 1990 p. 1319, 1633-1647.

Baker S G et al., Treatment of homozygous familial hypercholesterolaemia with probucol, *South African Medical Journal* (1982).

R. Milanese et al., Xantomi E Ipercolesterolemia: Prevalenza, Diagnosi e Terapia, *Chron. Derm.* 455-61 (1990).

Sorbera et al., Netoglitazone, *Drugs of the Future*, 2002, 27(2): 132-139.

Michel Farnier, Nouvelles approches médicamenteuses dans le traitement des dyslipidémies, *MT Endocrinologie*, 2002, 4:252-259.

Berger et al., Physiological and Therapeutic Roles of Peroxisome Proliferator-Activated Receptors, *Diabetes Technology & Therapeutics*, 2002, 4:163-174.

T. Kosoglou et al., "CoAdministration of Simvastatin and Ezetimibe Leads to Significant Reduction in LDL-Cholesterol", Proceedings of 3rd International Congress on Coronary, Artery Disease from Prevention to Intervention, Lyon, France p. 71 (2000), XP008027568.

Ashok K. Batta, et al., "Hydrophilic 7β-Hydroxy Bile Acids, Lovastatin, and Cholestyramine Are Ineffective in the Treatment of Cerebrotendinous Xanthomatosis" Metabolism, vol. 53, No. 5 pp. 556-562, 2004.

G. Salen, M.D. et al., "Ezetimibe Effectively Reduces Plasma Plant Sterols in Patiens With Sitosterolemia" Circulation, Clinical Investigation and Reports, pp. 966-971, 2004.

Akihiro Inazu et al., "Opposite effects on serum cholesteryl ester transfer protein levels between long-term treatments with pravastatin and probucol in patients with primary hypercholesterolemia and xanthoma" Atheroscierosis 145 pp. 405-413, 1999.

Gerald Salen et al., "Sitosterolemia" Journal of Lipid Research, vol. 33, pp. 945-955 1992.

\* cited by examiner

METHODS AND THERAPEUTIC COMBINATIONS FOR THE TREATMENT OF XANTHOMA USING STEROL ABSORPTION INHIBITORS

CROSS-REFERENCE TO RELATED APPLICATIONS

This application claims the benefit of priority from U.S. Provisional Patent Application Ser. No. 60/323,942, filed Sep. 21, 2001.

FIELD OF THE INVENTION

The present invention relates to methods and therapeutic combinations for treating and preventing xanthomas in a subject including the administration of certain sterol and/or 5α-stanol absorption inhibitors.

BACKGROUND OF THE INVENTION

Xanthomas are a common skin disorder associated with the accumulation of fatty materials under the surface of the skin. Xanthomas are most commonly associated with those who have high triglyceride and cholesterol levels.

Xanthoma is characterized by a lesion or bump that appears on the surface of the skin. Although the lesions or bumps are usually painless and soft to the touch, they are of a yellow color and may vary in size from very small up to a few inches, making them unsightly. Furthermore, the xanthoma itself may be indicative of an underlying disease such as diabetes, primary biliary cirrhosis, some types of cancer, or hypercholesterolemia.

Xanthomas, which are more specifically, benign fatty tumors, may be removed by surgical means, but if no other treatment is provided, they are likely to reform.

Therefore, there is a need for a method of treating and therapeutic combinations to treat xanthomas that not only reduce the incidence of xanthomas, but also prevent their formation.

SUMMARY OF THE INVENTION

In one embodiment, the present invention provides a method of preventing or decreasing the incidence of xanthomas in a subject comprising the step of administering to a subject in need of such treatment an effective amount of at least one sterol absorption inhibitor, at least one 5α-stanol absorption inhibitor, or a pharmaceutically acceptable salt or solvate thereof, to prevent or decrease the incidence of xanthomas in the subject.

In another embodiment, the present invention provides a method of preventing or decreasing the incidence of xanthomas in a subject comprising the step of administering to a subject in need of such treatment an effective amount of at least one sterol and/or 5α-stanol absorption inhibitor represented by Formulae I–XII below or a pharmaceutically acceptable salt or a solvate thereof to prevent or decrease the incidence of xanthomas in the subject.

Therapeutic combinations also are provided comprising: (a) a first amount of at least one sterol and/or 5α-stanol absorption inhibitor or a pharmaceutically acceptable salt or a solvate thereof; and (b) a second amount of at least one cholesterol biosynthesis inhibitor, wherein the first amount and the second amount together comprise a therapeutically effective amount for the treatment or prevention of xanthomas in a subject.

Other than in the operating examples, or where otherwise indicated, all numbers expressing quantities of ingredients, reaction conditions, and so forth used in the specification and claims are to be understood as being modified in all instances by the term "about".

DETAILED DESCRIPTION

In one embodiment, the present invention is directed to methods of treating or preventing xanthomas by administering an effective amount of a composition or a therapeutic combination comprising at least one (one or more) sterol absorption inhibitor(s) and/or at least one (one or more) 5α-stanol absorption inhibitor(s), such as but not limited to, substituted azetidinone or substituted β-lactam sterol absorption inhibitors discussed in detail below.

The term "therapeutically effective amount" means that amount of a therapeutic agent of the composition, such as the sterol and/or 5α-stanol absorption inhibitor(s) and other pharmacological or therapeutic agents described below, that will elicit a biological or medical response of a tissue, system, or subject that is being sought by the administrator (such as a researcher, doctor or veterinarian) which includes alleviation of the symptoms of the xanthoma condition or disease being treated and the prevention, slowing or halting of progression of the condition, including but not limited to decreasing the number of xanthomas and/or the size of the xanthomas.

Examples of suitable subjects that can be treated according to the methods of the present invention include mammals, such as humans or dogs, and other animals.

As used herein, "combination therapy" or "therapeutic combination" means the administration of two or more therapeutic agents, such as sterol or 5α-stanol absorption inhibitor(s) and other lipid lowering agents discussed below, such as cholesterol biosynthesis inhibitor(s), to prevent or treat xanthomas. Such administration includes coadministration of these therapeutic agents in a substantially simultaneous manner, such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating xanthomas. A potential advantage of the combination therapy disclosed herein may be a reduction in the required amount of an individual therapeutic compound or the overall total amount of therapeutic compounds that are effective in treating xanthomas. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

As discussed above, the compositions, pharmaceutical compositions and therapeutic combinations of the present invention comprise one or more sterol absorption inhibitors or 5α-stanol absorption inhibitors, such as for example substituted azetidinone or substituted β-lactam sterol absorption inhibitors discussed in detail below. As used herein, "sterol absorption inhibitor" means a compound capable of inhibiting the absorption of one or more sterols, including but not limited to cholesterol or phytosterols (such as sitosterol, campesterol, stigmasterol and avenosterol) when administered in a therapeutically effective (sterol absorption inhibiting) amount to a subject. "5α-stanol absorption inhibitor" means a compound capable of inhibiting the absorption of one or more 5α-stanols (such as cholestanol, 5α-campestanol, 5α-sitostanol) when administered in a therapeutically effective (5α-stanol absorption inhibiting) amount to a subject. Mixtures of sterol absorption inhibitor(s) and 5α-stanol absorption inhibitor(s) also are contemplated.

In a preferred embodiment, sterol or 5α-stanol absorption inhibitors useful in the compositions, therapeutic combinations and methods of the present invention are represented by Formula (I) below:

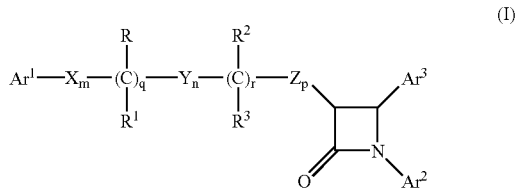

or a pharmaceutically acceptable salt thereof or a solvate thereof, wherein, in Formula (I) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(dilower alkyl)-;

R and $R^2$ are independently selected from the group consisting of —$OR^6$, —O(CO)$R^6$, —O(CO)O$R^9$ and —O(CO)N$R^6R^7$;

$R^1$ and $R^3$ are independently selected from the group consisting of hydrogen, lower alkyl and aryl;

q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1–5 substituents independently selected from the group consisting of lower alkyl, —$OR^6$, —O(CO)$R^6$, —O(CO)O$R^9$, —O($CH_2$)$_{1-5}$O$R^6$, —O(CO)N$R^6R^7$, —N$R^6R^7$, —N$R^6$(CO)$R^7$, —N$R^6$(CO)O$R^9$, —N$R^6$(CO)N$R^7R^8$, —N$R^6SO_2R^9$, —COO$R^6$, —CON$R^6R^7$, —COR$^6$, —$SO_2NR^6R^7$, $S(O)_{0-2}R^9$, —O($CH_2$)$_{1-10}$—COO$R^6$, —O($CH_2$)$_{1-10}$CON$R^6R^7$, -(lower alkylene)COO$R^6$, —CH═CH—COO$R^6$, —$CF_3$, —CN, —$NO_2$ and halogen;

$R^5$ is 1–5 substituents independently selected from the group consisting of —$OR^6$, —O(CO)$R^6$, —O(CO)O$R^9$, —O($CH_2$)$_{1-5}$O$R^6$, —O(CO)N$R^6R^7$, —N$R^6R^7$, —N$R^6$(CO) $R^7$, —N$R^6$(CO)O$R^9$, —N$R^6$(CO)N$R^7R^8$, —N$R^6SO_2R^9$, —COO$R^6$, —CON$R^6R^7$, —COR$^6$, —$SO_2NR^6R^7$, $S(O)_{0-2}$ $R^9$, —O($CH_2$)$_{1-10}$—COO$R^6$, —O($CH_2$)$_{1-10}$CON$R^6R^7$, -(lower alkylene)COO$R^6$ and —CH═CH—COO$R^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferably, $R^4$ is 1–3 independently selected substituents, and $R^5$ is preferably 1–3 independently selected substituents.

As used herein, the term "alkyl" or "lower alkyl" means straight or branched alkyl chains having from 1 to 6 carbon atoms and "alkoxy" means alkoxy groups having 1 to 6 carbon atoms. Non-limiting examples of lower alkyl groups include, for example methyl, ethyl, propyl, and butyl groups.

"Alkenyl" means straight or branched carbon chains having one or more double bonds in the chain, conjugated or unconjugated. Similarly, "alkynyl" means straight or branched carbon chains having one or more triple bonds in the chain. Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Aryl" means phenyl, naphthyl, indenyl, tetrahydronaphthyl or indanyl.

"Phenylene" means a bivalent phenyl group, including ortho, meta and para-substitution.

The statements wherein, for example, R, $R^1$, $R^2$ and $R^3$ are said to be independently selected from a group of substituents, mean that R, $R^1$, $R^2$ and $R^3$ are independently selected, but also that where an R, $R^1$, $R^2$ and $R^3$ variable occurs more than once in a molecule, each occurrence is independently selected (e.g., if R is —$OR^6$, wherein $R^6$ is hydrogen, $R^2$ can be —$OR^6$ wherein $R^6$ is lower alkyl). Those skilled in the art will recognize that the size and nature of the substituent(s) will affect the number of substituents that can be present.

Compounds of the invention have at least one asymmetrical carbon atom and therefore all isomers, including enantiomers, stereoisomers, rotamers, tautomers and racemates of the compounds of Formulae I–XII are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulas I–XII. Isomers may also include geometric isomers, e.g., when a double bond is present.

Those skilled in the art will appreciate that for some of the compounds of the Formulas I–XII, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

As used herein, "solvate" means a molecular or ionic complex of molecules or ions of solvent with those of solute (for example, one or more compounds of Formulae I–XII, isomers of the compounds of Formulae I–XII, or prodrugs of the compounds of Formulae I–XII). Non-limiting examples of useful solvents include polar, protic solvents such as water and/or alcohols (for example methanol).

Prodrugs of the compounds of Formulae I–XII are contemplated as being part of this invention. As used herein, "prodrug" means compounds that are drug precursors which, following administration to a patient, release the drug in vivo via some chemical or physiological process (e.g., a prodrug on being brought to the physiological pH or through enzyme action is converted to the desired drug form).

Preferred compounds of Formula (I) are those in which $Ar^1$ is phenyl or $R^4$-substituted phenyl, more preferably (4-$R^4$)-substituted phenyl. $Ar^2$ is preferably phenyl or $R^4$-substituted phenyl, more preferably (4-$R^4$)-substituted phenyl. $Ar^3$ is preferably $R^5$-substituted phenyl, more preferably (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or —$OR^6$ and $R^5$ is preferably —$OR^6$, wherein $R^6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably —$CH_2$—. $R^1$ and $R^3$ are each preferably hydrogen. R and $R^2$ are preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above).

The sum of m, n, p, q and r is preferably 2, 3 or 4, more preferably 3. Preferred are compounds wherein m, n and r are each zero, q is 1 and p is 2.

Also preferred are compounds of Formula (I) in which p, q and n are each zero, r is 1 and m is 2 or 3. More preferred are compounds wherein m, n and r are each zero, q is 1, p is 2, Z is —$CH_2$— and R is —$OR^6$, especially when $R^6$ is hydrogen.

Also more preferred are compounds of Formula (I) wherein p, q and n are each zero, r is 1, m is 2, X is —$CH_2$— and R is —$OR^6$, especially when $R^6$ is hydrogen.

Another group of preferred compounds of Formula (I) is that in which $Ar^1$ is phenyl or $R^4$-substituted phenyl, $Ar^2$ is phenyl or $R^4$-substituted phenyl and $Ar^3$ is $R^5$-substituted phenyl. Also preferred are compounds in which $Ar^1$ is phenyl or $R^4$-substituted phenyl, $Ar^2$ is phenyl or $R^4$-substituted phenyl, $Ar^3$ is $R^5$-substituted phenyl, and the sum of m, n, p, q and r is 2, 3 or 4, more preferably 3. More preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and wherein m, n and r are each zero, q is 1 and p is 2, or wherein p, q and n are each zero, r is 1 and m is 2 or 3.

In a preferred embodiment, a sterol or 5α-stanol absorption inhibitor of Formula (I) useful in the compositions, therapeutic combinations and methods of the present invention is represented by Formula (II) (ezetimibe) below:

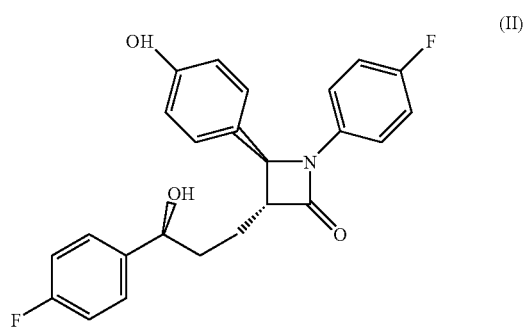

or a pharmaceutically acceptable salt or solvate thereof. The compound of Formula (II) can be in anhydrous or hydrated form.

Compounds of Formula I can be prepared by a variety of methods well known to those skilled in the art, for example such as are disclosed in U.S. Pat. Nos. 5,631,365, 5,767,115, 5,846,966, 6,207,822, U.S. patent application Ser. No. 10/105,710 filed Mar. 25, 2002, and PCT Patent Application WO 93/02048, each of which is incorporated herein by reference, and in the Example below. For example, suitable compounds of Formula I can be prepared by a method comprising the steps of:

(a) treating with a strong base a lactone of the Formula A or B:

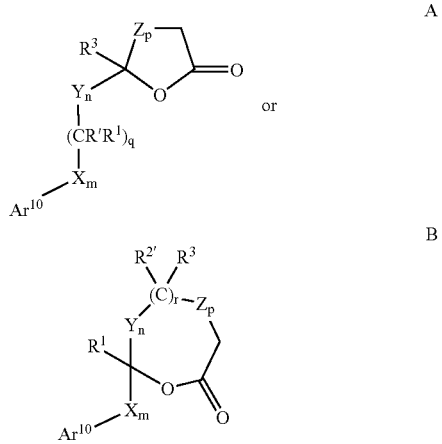

wherein R' and $R^{2'}$ are R and $R^2$, respectively, or are suitably protected hydroxy groups; $Ar^{10}$ is $Ar^1$, a suitably protected hydroxy-substituted aryl or a suitably protected amino-substituted aryl; and the remaining variables are as defined above for Formula I, provided that in lactone of formula B, when n and r are each zero, p is 1–4;

(b) reacting the product of step (a) with an imine of the formula

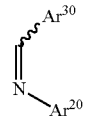

wherein $Ar^{20}$ is $Ar^2$, a suitably protected hydroxy-substituted aryl or a suitably protected amino-substituted aryl; and $Ar^{30}$ is $Ar^3$, a suitably protected hydroxy-substituted aryl or a suitably protected amino-substituted aryl;

c) quenching the reaction with an acid;

d) optionally removing the protecting groups from R', $R^{2'}$, $Ar^{10}$, $Ar^{20}$ and $Ar^{30}$, when present; and e) optionally functionalizing hydroxy or amino substituents at R, $R^2$, $Ar^1$, $Ar^2$ and $Ar^3$.

Using the lactones shown above, compounds of Formula IA and IB are obtained as follows:

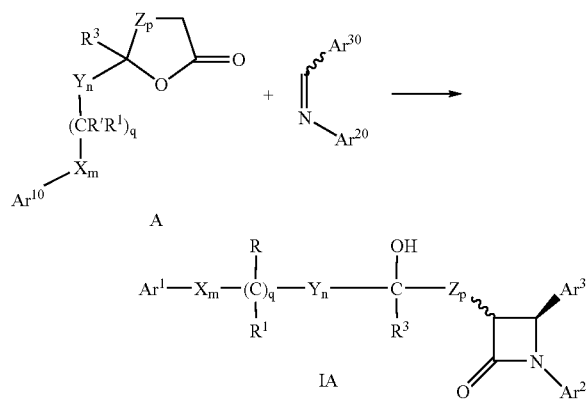

wherein the variables are as defined above; and

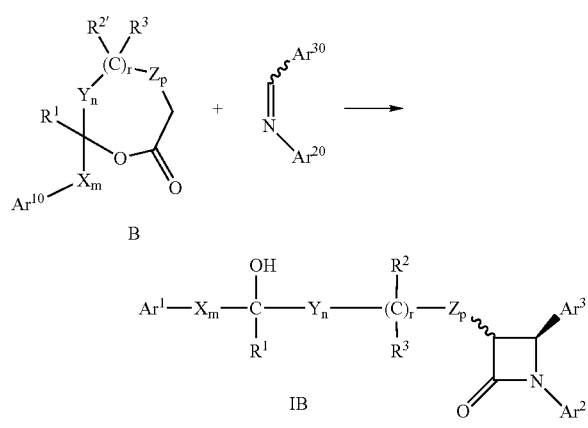

wherein the variables are as defined above.

Alternative sterol or 5α-stanol absorption inhibitors useful in the compositions, therapeutic combinations and methods of the present invention are represented by Formula (III) below:

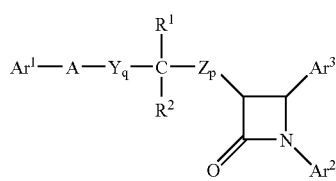

or a pharmaceutically acceptable salt thereof or a solvate thereof, wherein, in Formula (III) above:

$Ar^1$ is $R^3$-substituted aryl;
$Ar^2$ is $R^4$-substituted aryl;
$Ar^3$ is $R^5$-substituted aryl;

Y and Z are independently selected from the group consisting of —$CH_2$—, —CH(lower alkyl)- and —C(dilower alkyl)-;

A is selected from —O—, —S—, —S(O)— or —$S(O)_2$—;

$R^1$ is selected from the group consisting of —$OR^6$, —$O(CO)R^6$, —$O(CO)OR^9$ and —$O(CO)NR^6R^7$; $R^2$ is selected from the group consisting of hydrogen, lower alkyl and aryl; or $R^1$ and $R^2$ together are =O;

q is 1, 2 or 3;

p is 0, 1, 2, 3 or 4;

$R^5$ is 1–3 substituents independently selected from the group consisting of —$OR^6$, —$O(CO)R^6$, —$O(CO)OR^9$, —$O(CH_2)_{1-5}OR^9$, —$O(CO)NR^6R^7$, —$NR^6R^7$, —$NR^6(CO)R^7$, —$NR^6(CO)OR^9$, —$NR^6(CO)NR^7R^8$, —$NR^6SO_2$-lower alkyl, —$NR^6SO_2$-aryl, —$CONR^6R^7$, —$COR^6$, —$SO_2NR^6R^7$, $S(O)_{0-2}$-alkyl, $S(O)_{0-2}$-aryl, —$O(CH_2)_{1-10}$—$COOR^6$, —$O(CH_2)_{1-10}CONR^6R^7$, o-halogeno, m-halogeno, o-lower alkyl, m-lower alkyl, -(lower alkylene)-$COOR^6$, and —CH=CH—COOR;

$R^3$ and $R^4$ are independently 1–3 substituents independently selected from the group consisting of $R^5$, hydrogen, p-lower alkyl, aryl, —$NO_2$, —$CF_3$ and p-halogeno;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferred compounds of Formula I include those in which $Ar^1$ is $R^3$-substituted phenyl, especially (4-$R^3$)substituted phenyl. $Ar^2$ is preferably $R^4$-substituted phenyl, especially (4-$R^4$)-substituted phenyl. $Ar^3$ is preferably $R^5$-substituted phenyl, especially (4-$R^5$)-substituted phenyl. Mono-substitution of each of $Ar^1$, $Ar^2$ and $Ar^3$ is preferred.

Y and Z are each preferably —$CH_2$—. $R^2$ is preferably hydrogen. $R^1$ is preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above). Also preferred are compounds wherein $R^1$ and $R^2$ together are =O.

The sum of q and p is preferably 1 or 2, more preferably 1. Preferred are compounds wherein p is zero and q is 1. More preferred are compounds wherein p is zero, q is 1, Y is —$CH_2$— and R is —$OR^6$, especially when $R^6$ is hydrogen.

Another group of preferred compounds is that in which $Ar^1$ is $R^3$-substituted phenyl, $Ar^2$ is $R^4$-substituted phenyl and $Ar^3$ is $R^5$-substituted phenyl.

Also preferred are compounds wherein $Ar^1$ is $R^3$-substituted phenyl, $Ar^2$ is $R^4$-substituted phenyl, $Ar^3$ is $R^5$-substituted phenyl, and the sum of p and q is 1 or 2, especially 1. More preferred are compounds wherein $Ar^1$ is $R^3$-substituted phenyl, $Ar^2$ is $R^4$-substituted phenyl, $Ar^3$ is $R^5$-substituted phenyl, p is zero and q is 1.

A is preferably —O—.

$R^3$ is preferably —$COOR^6$, —$CONR^6R^7$, —$COR^6$, —$SO_2NR^6R^7$, $S(O)_{0-2}$-alkyl, $S(O)_{0-2}$-aryl, $NO_2$ or halogeno. A more preferred definition for $R^3$ is halogeno, especially fluoro or chloro.

$R^4$ is preferably hydrogen, lower alkyl, —$OR^6$, —$O(CO)R^6$, —$O(CO)OR^9$, —$O(CO)NR^6R^7$, —$NR^6R^7$, $COR^6$ or halogeno, wherein $R^6$ and $R^7$ are preferably independently hydrogen or lower alkyl, and $R^9$ is preferably lower alkyl. A more preferred definition for $R^4$ is hydrogen or halogeno, especially fluoro or chloro.

$R^5$ is preferably —$OR^6$, —$O(CO)R^6$, —$O(CO)OR^9$, —$O(CO)NR^6R^7$, —$NR^6R^7$, -(lower alkylene)-$COOR^6$ or —CH═CH—$COOR^6$, wherein $R^6$ and $R^7$ are preferably independently hydrogen or lower alkyl, and $R^9$ is preferably lower alkyl. A more preferred definition for $R^5$ is —$OR^6$, -(lower alkylene)-$COOR^6$ or —CH═CH—$COOR^6$, wherein $R^6$ is preferably hydrogen or lower alkyl.

Methods for making compounds of Formula III are well known to those skilled in the art. Non-limiting examples of suitable methods are disclosed in U.S. Pat. No. 5,688,990, which is incorporated herein by reference.

In another embodiment, sterol or 5α-stanol absorption inhibitors useful in the compositions, therapeutic combinations and methods of the present invention are represented by Formula (IV):

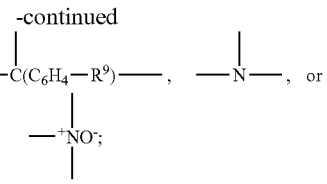

(IV)

or a pharmaceutically acceptable salt thereof or a solvate thereof, wherein, in Formula (IV) above:

A is selected from the group consisting of $R^2$-substituted heterocycloalkyl, $R^2$-substituted heteroaryl, $R^2$-substituted benzofused heterocycloalkyl, and $R^2$-substituted benzofused heteroaryl;

$Ar^1$ is aryl or $R^3$-substituted aryl;

$Ar^2$ is aryl or $R^4$-substituted aryl;

Q is a bond or, with the 3-position ring carbon of the azetidinone, forms the spiro group

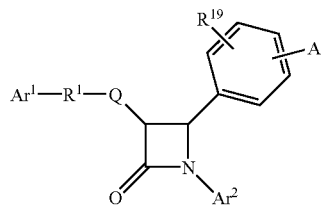

and $R^1$ is selected from the group consisting of:

—$(CH_2)_q$—, wherein q is 2–6, provided that when Q forms a spiro ring, q can also be zero or 1;

—$(CH_2)_e$-G-$(CH_2)_r$—, wherein G is —O—, —C(O)—, phenylene, —$NR^8$— or —$S(O)_{0-2}$—, e is 0–5 and r is 0–5, provided that the sum of e and r is 1–6;

—($C_2$–$C_6$ alkenylene)-; and

—$(CH_2)_f$—V—$(CH_2)_g$—, wherein V is $C_3$–$C_6$ cycloalkylene, f is 1–5 and g is 0–5, provided that the sum of f and g is 1–6;

$R^5$ is selected from:

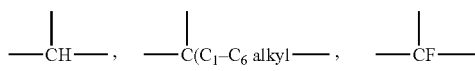

-continued

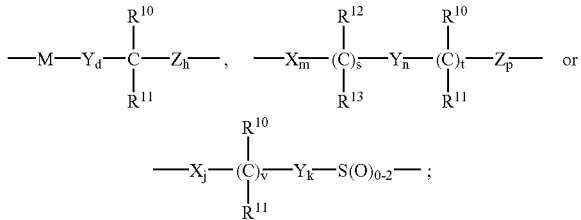

$R^6$ and $R^7$ are independently selected from the group consisting of —$CH_2$—, —CH($C_1$–$C_6$ alkyl)-, —C(di-($C_1$–$C_6$)alkyl), —CH═CH— and —C($C_1$–$C_6$ alkyl)═CH—; or $R^5$ together with an adjacent $R^6$, or $R^5$ together with an adjacent $R^7$, form a —CH═CH— or a —CH═C($C_1$–$C_6$ alkyl)- group;

a and b are independently 0, 1, 2 or 3, provided both are not zero; provided that when $R^6$ is —CH═CH— or —C($C_1$–$C_6$ alkyl)═CH—, a is 1; provided that when $R^7$ is —CH═CH— or —C($C_1$–$C_6$ alkyl)═CH—, b is 1; provided that when a is 2 or 3, the $R^6$'s can be the same or different; and provided that when b is 2 or 3, the $R^7$'s can be the same or different;

and when Q is a bond, $R^1$ also can be selected from:

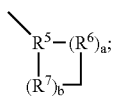

where M is —O—, —S—, —S(O)— or —$S(O)_2$—;

X, Y and Z are independently selected from the group consisting of —$CH_2$—, —CH($C_1$–$C_6$ alkyl)- and —C(di-($C_1$–$C_6$) alkyl);

$R^{10}$ and $R^{12}$ are independently selected from the group consisting of —$OR^{14}$, —$O(CO)R^{14}$, —$O(CO)OR^{16}$ and —$O(CO)NR^{14}R^{15}$;

$R^{11}$ and $R^{13}$ are independently selected from the group consisting of hydrogen, ($C_1$–$C_6$)alkyl and aryl; or $R^{10}$ and $R^{11}$ together are ═O, or $R^{12}$ and $R^{13}$ together are ═O;

d is 1, 2 or 3;

h is 0, 1, 2, 3 or 4;

s is 0 or 1; t is 0 or 1; m, n and p are independently 0–4; provided that at least one of s and t is 1, and the sum of m, n, p, s and t is 1–6; provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

$R^2$ is 1–3 substituents on the ring carbon atoms selected from the group consisting of hydrogen, ($C_1$–$C_{10}$)alkyl, ($C_2$–$C_{10}$)alkenyl, ($C_2$–$C_{10}$)alkynyl, ($C_3$–$C_6$)cycloalkyl, ($C_3$–$C_6$)cycloalkenyl, $R^{17}$-substituted aryl, $R^{17}$-substituted benzyl, $R^{17}$-substituted benzyloxy, $R^{17}$-substituted aryloxy, halogeno, —$NR^{14}R^{15}$, $NR^{14}R^{15}$($C_1$–$C_6$ alkylene)-, $NR^{14}R^{15}C(O)(C_1$–$C_6$ alkylene)-, —$NHC(O)R^{16}$, OH, $C_1$–$C_6$ alkoxy, —$OC(O)R^{16}$, —$COR^{14}$, hydroxy($C_1$–$C_6$)alkyl, ($C_1$–$C_6$)alkoxy($C_1$–$C_6$) alkyl, $NO_2$, —$S(O)_{0-2}R^{16}$, —$SO_2NR^{14}R^{15}$ and —$(C_1$–$C_6$alkylene)$COOR^{14}$; when $R^2$ is a substituent on a heterocycloalkyl ring, $R^2$ is as defined, or is =O or

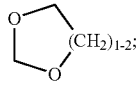

and, where $R^2$ is a substituent on a substitutable ring nitrogen, it is hydrogen, $(C_1$–$C_6)$alkyl, aryl, $(C_1$–$C_6)$alkoxy, aryloxy, $(C_1$–$C_6)$alkylcarbonyl, arylcarbonyl, hydroxy, —$(CH_2)_{1-6}CONR^{18}R^{18}$,

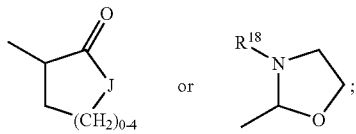

wherein J is —O—, —NH—, —$NR^{18}$— or —$CH_2$—;

$R^3$ and $R^4$ are independently selected from the group consisting of 1–3 substituents independently selected from the group consisting of $(C_1$–$C_6)$alkyl, —$OR^{14}$, —$O(CO)R^{14}$, —$O(CO)OR^{16}$, —$O(CH_2)_{1-5}OR^{14}$, —$O(CO)NR^{14}R^{15}$, —$NR^{14}R^{15}$, —$NR^{14}(CO)R^{15}$, —$NR^{14}(CO)OR^{16}$, —$NR^{14}(CO)NR^{15}R^{19}$, —$NR^{14}SO_2R^{16}$, —$COOR^{14}$, —$CONR^{14}R^{15}$, —$COR^{14}$, —$SO_2NR^{14}R^{15}$, $S(O)_{0-2}R^{16}$, —$O(CH_2)_{1-10}$—$COOR^{14}$, —$O(CH_2)_{1-10}CONR^{14}R^{15}$, —$(C_1$–$C_6$alkylene)-$COOR^{14}$, —CH=CH—$COOR^{14}$, —$CF_3$, —CN, —$NO_2$ and halogen;

$R^8$ is hydrogen, $(C_1$–$C_6)$alkyl, aryl $(C_1$–$C_6)$alkyl, —$C(O)R^{14}$ or —$COOR^{14}$;

$R^9$ and $R^{17}$ are independently 1–3 groups independently selected from the group consisting of hydrogen, $(C_1$–$C_6)$alkyl, $(C_1$–$C_6)$alkoxy, —COOH, $NO_2$, —$NR^{14}R^{15}$, OH and halogeno;

$R^{14}$ and $R^{15}$ are independently selected from the group consisting of hydrogen, $(C_1$–$C_6)$alkyl, aryl and aryl-substituted $(C_1$–$C_6)$alkyl;

$R^{16}$ is $(C_1$–$C_6)$alkyl, aryl or $R^{17}$-substituted aryl;

$R^{18}$ is hydrogen or $(C_1$–$C_6)$alkyl; and $R^{19}$ is hydrogen, hydroxy or $(C_1$–$C_6)$alkoxy.

As used in Formula (IV) above, "A" is preferably an $R^2$-substituted, 6-membered heterocycloalkyl ring containing 1 or 2 nitrogen atoms. Preferred heterocycloalkyl rings are piperidinyl, piperazinyl and morpholinyl groups. The ring "A" is preferably joined to the phenyl ring through a ring nitrogen. Preferred $R^2$ substituents are hydrogen and lower alkyl. $R^{19}$ is preferably hydrogen.

$Ar^2$ is preferably phenyl or $R^4$-phenyl, especially (4-$R^4$)-substituted phenyl. Preferred definitions of $R^4$ are lower alkoxy, especially methoxy, and halogeno, especially fluoro.

$Ar^1$ is preferably phenyl or $R^3$-substituted phenyl, especially (4-$R^3$)-substituted phenyl.

There are several preferred definitions for the —$R^1$-Q- combination of variables:

Q is a bond and $R^1$ is lower alkylene, preferably propylene;

Q is a spiro group as defined above, wherein preferably $R^6$ and $R^7$ are each ethylene and $R^5$ is

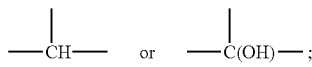

Q is a bond and $R^1$ is

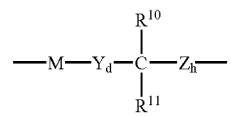

wherein the variables are chosen such that $R^1$ is —O—$CH_2$—CH(OH)—;

Q is a bond and $R^1$ is

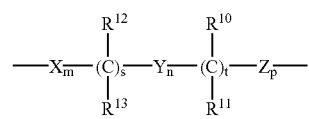

wherein the variables are chosen such that $R^1$ is —CH(OH)—$(CH_2)_2$—; and

Q is a bond and $R^1$ is

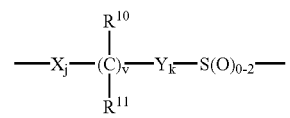

wherein the variables are chosen such that $R^1$ is —CH(OH)—$CH_2$—$S(O)_{0-2}$—.

Methods for making compounds of Formula IV are well known to those skilled in the art. Non-limiting examples of suitable methods are disclosed in U.S. Pat. No. 5,656,624, which is incorporated herein by reference.

In another embodiment, sterol or 5α-stanol absorption inhibitors useful in the compositions, therapeutic combinations and methods of the present invention are represented by Formula (V):

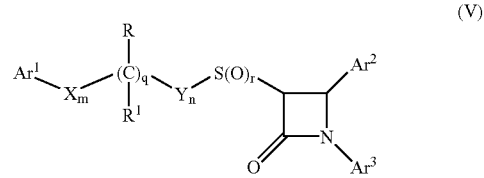

or a pharmaceutically acceptable salt thereof or a solvate thereof, wherein, in Formula (V) above:

$Ar^1$ is aryl, $R^{10}$-substituted aryl or heteroaryl;

$Ar^2$ is aryl or $R^4$-substituted aryl;

$Ar^3$ is aryl or $R^5$-substituted aryl;

X and Y are independently selected from the group consisting of —$CH_2$—, —CH(lower alkyl)- and —C(dilower alkyl)-;

R is —OR$^6$, —O(CO)R$^6$, —O(CO)OR$^9$ or —O(CO)NR$^6$R$^7$; R$^1$ is hydrogen, lower alkyl or aryl; or R and R$^1$ together are =O;

q is 0 or 1;

r is 0, 1 or 2;

m and n are independently 0, 1, 2, 3, 4 or 5; provided that the sum of m, n and q is 1, 2, 3, 4 or 5;

R$^4$ is 1–5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene)COOR$^6$ and —CH=CH—COOR$^6$;

R$^5$ is 1–5 substituents independently selected from the group consisting of —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, —CF$_3$, —CN, —NO$_2$, halogen, -(lower alkylene)COOR$^6$ and —CH=CH—COOR$^6$;

R$^6$, R$^7$ and R$^8$ are independently selected from the group consisting of hydrogen, lower alkyl, aryl and aryl-substituted lower alkyl;

R$^9$ is lower alkyl, aryl or aryl-substituted lower alkyl; and

R$^{10}$ is 1–5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, —S(O)$_{0-2}$R$^9$, —O(CH$_2$)$_{1-10}$—COOR$^6$, —O(CH$_2$)$_{1-10}$CONR$^6$R$^7$, —CF$_3$, —CN, —NO$_2$ and halogen.

Within the scope of Formula V, there are included two preferred structures. In Formula VA, q is zero and the remaining variables are as defined above, and in Formula VB, q is 1 and the remaining variables are as defined above:

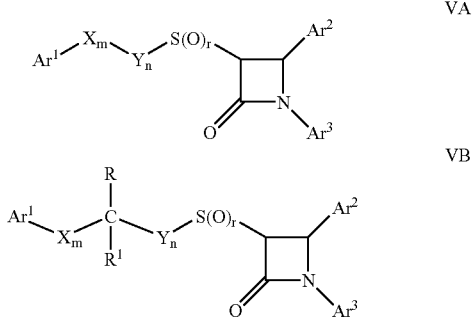

R$^4$, R$^5$ and R$^{10}$ are each preferably 1–3 independently selected substituents as set forth above. Preferred are compounds of Formula (V) wherein Ar$^1$ is phenyl, R$^{10}$-substituted phenyl or thienyl, especially (4-R$^{10}$)-substituted phenyl or thienyl. Ar$^2$ is preferably R$^4$-substituted phenyl, especially (4-R$^4$)-substituted phenyl. Ar$^3$ is preferably phenyl or R$^5$-substituted phenyl, especially (4-R$^5$)-substituted phenyl. When Ar$^1$ is R$^{10}$-substituted phenyl, R$^{10}$ is preferably halogeno, especially fluoro. When Ar$^2$ is R$^4$-substituted phenyl, R$^4$ is preferably —OR$^6$, especially wherein R$^6$ is hydrogen or lower alkyl. When Ar$^3$ is R$^5$-substituted phenyl, R$^5$ is preferably halogeno, especially fluoro. Especially preferred are compounds of Formula (V) wherein Ar$^1$ is phenyl, 4-fluorophenyl or thienyl, Ar$^2$ is 4-(alkoxy or hydroxy)phenyl, and Ar$^3$ is phenyl or 4-fluorophenyl.

X and Y are each preferably —CH$_2$—. The sum of m, n and q is preferably 2, 3 or 4, more preferably 2. When q is 1, n is preferably 1 to 5.

Preferences for X, Y, Ar$^1$, Ar$^2$ and Ar$^3$ are the same in each of Formulae (VA) and (VB).

In compounds of Formula (VA), the sum of m and n is preferably 2, 3 or 4, more preferably 2. Also preferred are compounds wherein the sum of m and n is 2, and r is 0 or 1.

In compounds of Formula (VB), the sum of m and n is preferably 1, 2 or 3, more preferably 1. Especially preferred are compounds wherein m is zero and n is 1. R$^1$ is preferably hydrogen and R is preferably —OR$^6$ wherein R$^6$ is hydrogen, or a group readily metabolizable to a hydroxyl (such as —O(CO)R$^6$, —O(CO)OR$^9$ and —O(CO)NR$^6$R$^7$, defined above), or R and R$^1$ together form a =O group.

Methods for making compounds of Formula V are well known to those skilled in the art. Non-limiting examples of suitable methods are disclosed in U.S. Pat. No. 5,624,920, which is incorporated herein by reference.

In another embodiment, sterol or 5α-stanol absorption inhibitors useful in the compositions, therapeutic combinations and methods of the present invention are represented by Formula (VI):

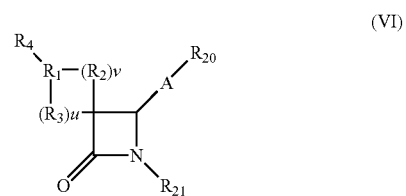

or a pharmaceutically acceptable salt thereof or a solvate thereof, wherein:

R$_1$ is

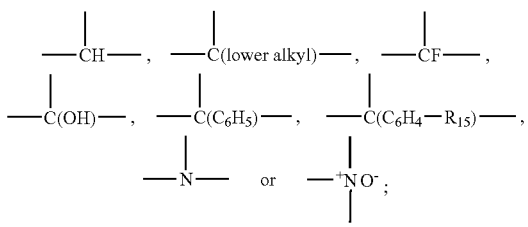

R$_2$ and R$_3$ are independently selected from the group consisting of: —CH$_2$—, —CH(lower alkyl)-, —C(di-lower alkyl)-, —CH=CH— and —C(lower alkyl)=CH—; or R$_1$ together with an adjacent R$_2$, or R$_1$ together with an adjacent R$_3$, form a —CH=CH— or a —CH=C(lower alkyl)- group;

u and v are independently 0, 1, 2 or 3, provided both are not zero; provided that when R$_2$ is —CH=CH— or —C(lower alkyl)=CH—, v is 1; provided that when R$_3$ is —CH=CH— or —C(lower alkyl)=CH—, u is 1; provided that when v is 2 or 3, the R$_2$'s can be the same or different; and provided that when u is 2 or 3, the R$_3$'s can be the same or is different;

$R_4$ is selected from B—$(CH_2)_mC(O)$—, wherein m is 0, 1, 2, 3, 4 or 5; B—$(CH_2)_q$—, wherein q is 0, 1, 2, 3, 4, 5 or 6; B—$(CH_2)_e$-Z-$(CH_2)_r$—, wherein Z is —O—, —C(O)—, phenylene, —N($R_8$)— or —S(O)$_{0-2}$—, e is 0, 1, 2, 3, 4 or 5 and r is 0, 1, 2, 3, 4 or 5, provided that the sum of e and r is 0, 1, 2, 3, 4, 5 or 6; B-($C_2$–$C_6$ alkenylene)-; B—($C_4$–$C_6$ alkadienylene)-; B—$(CH_2)_t$-Z-($C_2$–$C_6$ alkenylene)-, wherein Z is as defined above, and wherein t is 0, 1, 2 or 3, provided that the sum of t and the number of carbon atoms in the alkenylene chain is 2, 3, 4, 5 or 6; B—$(CH_2)_f$—V—$(CH_2)_g$—, wherein V is C3–$C_6$ cycloalkylene, f is 1, 2, 3, 4 or 5 and g is 0, 1, 2, 3, 4 or 5, provided that the sum of f and g is 1, 2, 3, 4, 5 or 6; B—$(CH_2)_t$—V—($C_2$–$C_6$ alkenylene)- or B—($C_2$–$C_6$ alkenylene)-V—$(CH_2)_t$—, wherein V and t are as defined above, provided that the sum of t and the number of carbon atoms in the alkenylene chain is 2, 3, 4, 5 or 6;

B—$(CH_2)_a$-Z-$(CH_2)_b$—V—$(CH_2)_d$—, wherein Z and V are as defined above and a, b and d are independently 0, 1, 2, 3, 4, 5 or 6, provided that the sum of a, b and d is 0, 1, 2, 3, 4, 5 or 6; or T-$(CH_2)_s$—, wherein T is cycloalkyl of 3–6 carbon atoms and s is 0, 1, 2, 3, 4, 5 or 6; or $R_1$ and $R_4$ together form the group B—CH=C—;

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

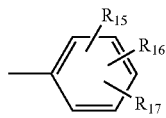

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —$CF_3$, —$OCF_3$, benzyl, $R_7$-benzyl, benzyloxy, $R_7$-benzyloxy, phenoxy, $R_7$-phenoxy, dioxolanyl, $NO_2$, —N($R_8$)($R_9$), N($R_8$)($R_9$)-lower alkylene-, N($R_8$)($R_9$)-lower alkylenyloxy-, OH, halogeno, —CN, —$N_3$, —NHC(O)O$R_{10}$, —NHC(O)$R_{10}$, $R_{11}O_2$SNH—, ($R_{11}O_2$S)$_2$N—, —S(O)$_2$NH$_2$, —S(O)$_{0-2}R_8$, tert-butyldimethyl-silyloxymethyl, —C(O)$R_{12}$, —COO$R_{19}$, —CON($R_8$)($R_9$), —CH=CHC(O)$R_{12}$, -lower alkylene-C(O)$R_{12}$, $R_{10}$C(O)(lower alkylenyloxy)-, N($R_8$)($R_9$)C(O)(lower alkylenyloxy)- and

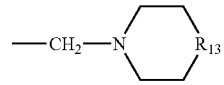

for substitution on ring carbon atoms, and the substituents on the substituted heteroaryl ring nitrogen atoms, when present, are selected from the group consisting of lower alkyl, lower alkoxy, —C(O)O$R_{10}$, —C(O)$R_{10}$, OH, N($R_8$)($R_9$)-lower alkylene-, N($R_8$)($R_9$)-lower alkylenyloxy-, —S(O)$_2$NH$_2$ and 2-(trimethylsilyl)-ethoxymethyl;

$R_7$ is 1–3 groups independently selected from the group consisting of lower alkyl, lower alkoxy, —COOH, $NO_2$, —N($R_8$)($R_9$), OH, and halogeno;

$R_8$ and $R_9$ are independently selected from H or lower alkyl;

$R_{10}$ is selected from lower alkyl, phenyl, $R_7$-phenyl, benzyl or $R_7$-benzyl;

$R_{11}$ is selected from OH, lower alkyl, phenyl, benzyl, $R_7$-phenyl or $R_7$-benzyl;

$R_{12}$ is selected from H, OH, alkoxy, phenoxy, benzyloxy,

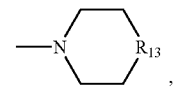

—N($R_8$)($R_9$), lower alkyl, phenyl or $R_7$-phenyl;

$R_{13}$ is selected from —O—, —$CH_2$—, —NH—, —N(lower alkyl)- or —NC(O)$R_{19}$;

$R_{15}$, $R_{16}$ and $R_{17}$ are independently selected from the group consisting of H and the groups defined for W; or $R_{15}$ is hydrogen and $R_{16}$ and $R_{17}$, together with adjacent carbon atoms to which they are attached, form a dioxolanyl ring;

$R_{19}$ is H, lower alkyl, phenyl or phenyl lower alkyl; and $R_{20}$ and $R_{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzofused heteroaryl and cyclopropyl, wherein heteroaryl is as defined above.

One group of preferred compounds of Formula VI is that in which $R_{21}$ is selected from phenyl, W-substituted phenyl, indanyl, benzofuranyl, benzodioxolyl, tetrahydronaphthyl, pyridyl, pyrazinyl, pyrimidinyl, quinolyl or cyclopropyl, wherein W is lower alkyl, lower alkoxy, OH, halogeno, —N($R_8$)($R_9$), —NHC(O)O$R_{10}$, —NHC(O)$R_{10}$, $NO_2$, —CN, —$N_3$, —SH, —S(O)$_{0-2}$-(lower alkyl), —COO$R_{19}$, —CON($R_8$)($R_9$), —COR$_{12}$, phenoxy, benzyloxy, —OCF$_3$, —CH=C(O)$R_{12}$ or tert-butyldimethylsilyloxy, wherein $R_8$, $R_9$, $R_{10}$, $R_{12}$ and $R_{19}$ are as defined for Formula IV. When W is 2 or 3 substituents, the substituents can be the same or different.

Another group of preferred compounds of Formula VI is that in which $R_{20}$ is phenyl or W-substituted phenyl, wherein preferred meanings of W are as defined above for preferred definitions of $R_{21}$.

More preferred are compounds of Formula VI wherein $R_{20}$ is phenyl or W-substituted phenyl and $R_{21}$ is phenyl, W-substituted phenyl, indanyl, benzofuranyl, benzodioxolyl, tetrahydronaphthyl, pyridyl, pyrazinyl, pyrimidinyl, quinolyl or cyclopropyl; W is lower alkyl, lower alkoxy, OH, halogeno, —N(R8)($R_9$), —NHC(O)O$R_{10}$, —NHC(O)$R_{10}$, $NO_2$, —CN, —$N_3$, —SH, —S(O)$_{0-2}$-(lower alkyl), —COO$R_{19}$, —CON($R_8$)($R_9$), —COR$_{12}$, phenoxy, benzyloxy, —CH=CHC(O)$R_{12}$, —OCF$_3$ or tert-butyl-dimethylsilyloxy, wherein when W is 2 or 3 substituents, the substituents can be the same or different, and wherein $R_8$, $R_9$, $R_{10}$, $R_{12}$ and $R_{19}$ are as defined in Formula VI.

Also preferred are compounds of Formula VI wherein $R_1$ is —CH— or —C(OH)—.

Another group of preferred compounds of Formula VI is in which $R_2$ and $R_3$ are each —$CH_2$— and the sum of u and v is 2, 3 or 4, with u=v=2 being more preferred.

$R_4$ is preferably B—$(CH_2)_q$— or B—$(CH_2)_e$-Z-$(CH_2)_r$—, wherein B, Z, q, e and r are as defined above. B is preferably

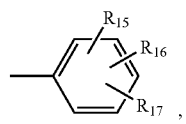

wherein $R_{16}$ and $R_{17}$ are each hydrogen and wherein $R_{15}$ is preferably H, OH, lower alkoxy, especially methoxy, or halogeno, especially chloro.

Preferably Z is —O—, e is 0, and r is 0.

Preferably q is 0–2.

$R_{20}$ is preferably phenyl or W-substituted phenyl.

Preferred W substituents for $R_{20}$ are lower alkoxy, especially methoxy and ethoxy, OH, and —C(O)$R_{12}$, wherein $R_{12}$ is preferably lower alkoxy.

Preferably $R_{21}$ is selected from phenyl, lower alkoxy-substituted phenyl and F-phenyl.

Especially preferred are compounds of Formula VI wherein $R_1$ is —CH—, or —C(OH)—, $R_2$ and $R_3$ are each —CH$_2$—, u=v=2, $R_4$ is B—(CH$_2$)$_q$—, wherein B is phenyl or phenyl substituted by lower alkoxy or chloro, q is 0–2, $R_{20}$ is phenyl, OH-phenyl, lower alkoxy-substituted phenyl or lower alkoxycarbonyl-substituted phenyl, and $R_{21}$ is phenyl, lower alkoxy-substituted phenyl or F-phenyl.

Methods for making compounds of Formula VI are well known to those skilled in the art. Non-limiting examples of suitable methods are disclosed in U.S. Pat. No. 5,698,548, which is incorporated herein by reference.

In another embodiment, sterol or 5α-stanol absorption inhibitors useful in the compositions, therapeutic combinations and methods of the present invention are represented by Formulas (VIIA) and (VIIB):

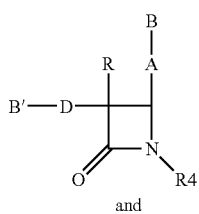
(VIIA)

and

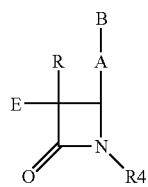
(VIIB)

or a pharmaceutically acceptable salt or solvate thereof, wherein:

A is —CH=CH—, —C≡C— or —(CH$_2$)$_p$— wherein p is 0, 1 or 2;

B is

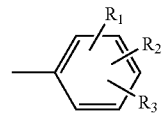

B' is

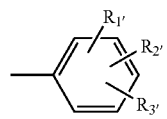

D is —(CH$_2$)$_m$C(O)— or —(CH$_2$)$_q$— wherein m is 1, 2, 3 or 4 and q is 2, 3 or 4;

E is $C_{10}$ to $C_{20}$ alkyl or —C(O)—($C_9$ to $C_{19}$)-alkyl, wherein the alkyl is straight or branched, saturated or containing one or more double bonds;

R is hydrogen, $C_1$–$C_{15}$ alkyl, straight or branched, saturated or containing one or more double bonds, or B—(CH$_2$)$_r$—, wherein r is 0, 1, 2, or 3;

$R_1$, $R_2$, $R_3$, $R_{1'}$, $R_{2'}$, and $R_{3'}$ are independently selected from the group consisting of hydrogen, lower alkyl, lower alkoxy, carboxy, NO$_2$, NH$_2$, OH, halogeno, lower alkylamino, dilower alkylamino, —NHC(O)OR$_5$, $R_6O_2$SNH— and —S(O)$_2$NH$_2$;

$R_4$ is

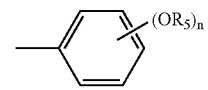

wherein n is 0, 1, 2 or 3;

$R_5$ is lower alkyl; and $R_6$ is OH, lower alkyl, phenyl, benzyl or substituted phenyl wherein the substituents are 1–3 groups independently selected from the group consisting of lower alkyl, lower alkoxy, carboxy, NO$_2$, NH$_2$, OH, halogeno, lower alkylamino and dilower alkylamino; or a pharmaceutically acceptable salt thereof or a prodrug thereof.

Preferred are compounds of Formula (VIIA) wherein R is hydrogen, saturated or mono-unsaturated $C_1$–$C_{10}$ alkyl or phenyl. Another group of preferred compounds of Formula (VIIA) is that in which D is propyl (i.e., —(CH$_2$)$_q$— and q is 3). A third group of preferred compounds of Formula (VIIA) is that wherein R4 is p-methoxyphenyl or 2,4,6-trimethoxyphenyl. Still another group of preferred compounds of Formula (VIIA) is that wherein A is ethylene or a bond (i.e., —(CH$_2$)$_p$— wherein p is zero). $R_{1'}$, $R_{2'}$, and $R_{3'}$, are preferably each hydrogen, and preferably $R_1$ is hydrogen, hydroxy, nitro, lower alkoxy, amino or t-butoxycarbonyl-amino and $R_2$ and $R_3$ are each hydrogen.

More preferred are compounds of Formula (VIIA) wherein $R_{1'}$, $R_{2'}$, and $R_{3'}$ are each hydrogen; $R_1$ is hydrogen, hydroxy, nitro, lower alkoxy, amino or t-butoxycarbonyl-amino and $R_2$ and $R_3$ are each hydrogen; R is hydrogen, ethyl or phenyl; D is propyl; $R_4$ is p-methoxyphenyl or 2,4,6-trimethoxyphenyl; and A is ethylene or a bond.

Preferred compounds of Formula (VIIA), wherein B' is phenyl, are shown in the following table:

| D | R | A | B | R$_4$ |
|---|---|---|---|---|
| —(CH$_2$)$_3$— | H | — | p-MeO-phenyl | p-MeO-phenyl |
| —CH$_2$C(O)— | phenyl | — | phenyl | p-MeO-phenyl |
| —(CH$_2$)$_3$— | H | — | phenyl | p-MeO-phenyl |
| —(CH$_2$)$_3$— | H | — | p-OH-phenyl | p-MeO-phenyl |
| —(CH$_2$)$_3$— | H | ethylene | p-MeO-phenyl | p-MeO-phenyl |
| —(CH$_2$)$_3$— | H | — | 3-MeO-phenyl | p-MeO-phenyl |
| —(CH$_2$)$_3$— | ethyl | — | phenyl | p-MeO-phenyl |
| —(CH$_2$)$_3$— | phenyl | — | phenyl | p-MeO-phenyl |
| —(CH$_2$)$_3$— | ethyl | — | phenyl | 2,4,6-tri-MeO-phenyl |
| —(CH$_2$)$_3$— | methyl | — | phenyl | p-MeO-phenyl |
| —(CH$_2$)$_3$— | H | — | p-NH$_2$-phenyl | p-MeO-phenyl |

The first-listed compound in the above table having the (3R,4S) absolute stereochemistry is more preferred.

Preferred compounds of Formula (VIIB) are those wherein R is hydrogen, methyl, ethyl, phenyl or phenylpropyl. Another group of preferred compounds of Formula (VIIB) is that wherein R$_4$ is p-methoxyphenyl or 2,4,6-trimethoxyphenyl. Still another group of preferred compounds of Formula (VIB) is that wherein A is ethylene or a bond. Yet another group of preferred compounds of Formula (VIIB) is that wherein E is decyl, oleoyl or 7-Z-hexadecenyl. Preferably R$_1$, R$_2$ and R$_3$ are each hydrogen.

More preferred compounds of Formula (VIIB) are those wherein R is hydrogen, methyl, ethyl, phenyl or phenylpropyl; R$_4$ is p-methoxyphenyl or 2,4,6-trimethoxyphenyl; A is ethylene or a bond; E is decyl, oleoyl or 7-Z-hexadecenyl; and R$_1$, R$_2$ and R$_3$ are each hydrogen.

A preferred compound of Formula (VIIB) is that wherein E is decyl, R is hydrogen, B-A is phenyl and R$_4$ is p-methoxyphenyl.

In another embodiment, sterol or 5α-stanol absorption inhibitors useful in the compositions and methods of the present invention are represented by Formula (VIII):

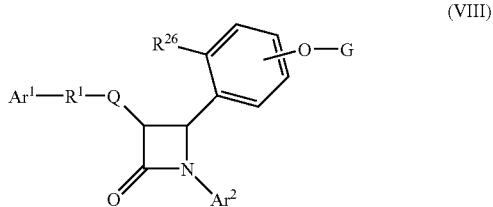

(VIII)

or a pharmaceutically acceptable salt thereof or a solvate thereof, wherein, in Formula (VIII) above, R$^{26}$ is H or OG$^1$;

G and G$^1$ are independently selected from the group consisting of

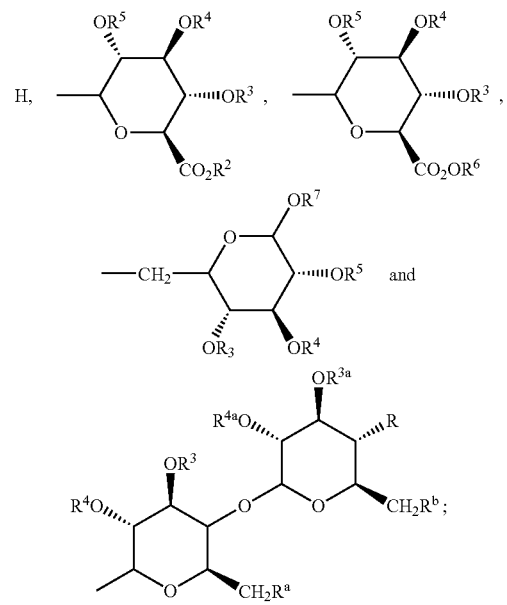

provided that when R$^{26}$ is H or OH, G is not H;

R, R$^a$ and R$^b$ are independently selected from the group consisting of H, —OH, halogeno, —NH$_2$, azido, (C$_1$–C$_6$)alkoxy(C$_1$–C$_6$)-alkoxy or —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

R$^2$ and R$^6$ are independently selected from the group consisting of H, (C$_1$–C$_6$)alkyl, aryl and aryl(C$_1$–C$_6$)alkyl;

R$^3$, R$^4$, R$^5$, R$^7$, R$^{3a}$ and R$^{4a}$ are independently selected from the group consisting of H, (C$_1$–C$_6$)alkyl, aryl(C$_1$–C$_6$)alkyl, —C(O)(C$_1$–C$_6$)alkyl and —C(O)aryl;

R$^{30}$ is selected from the group consisting of R$^{32}$-substituted T, R$^{32}$-substituted-T-(C$_1$–C$_6$)alkyl, R$^{32}$-substituted-(C$_2$–C$_4$)alkenyl, R$^{32}$-substituted-(C$_1$–C$_6$)alkyl, R$^{32}$-substituted-(C$_3$–C$_7$)cycloalkyl and R$^{32}$-substituted-(C$_3$–C$_7$)cycloalkyl (C$_1$–C$_6$)alkyl;

R$^{31}$ is selected from the group consisting of H and (C$_1$–C$_4$)alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

R$^{32}$ is independently selected from 1–3 substituents independently selected from the group consisting of halogeno, (C$_1$–C$_4$)alkyl, —OH, phenoxy, —CF$_3$, —NO$_2$, (C$_1$–C$_4$)alkoxy, methylenedioxy, oxo, (C$_1$–C$_4$)alkylsulfanyl, (C$_1$–C$_4$)alkylsulfinyl, (C$_{1-C4}$)alkylsulfonyl, —N(CH$_3$)$_2$, —C(O)—NH(C$_{1-C4}$)alkyl, —C(O)—N((C$_1$–C$_4$)alkyl)$_2$, —C(O)—(C$_1$–C$_4$)alkyl, —C(O)—(C$_1$–C$_4$)alkoxy and pyrrolidinylcarbonyl; or R$^{32}$ is a covalent bond and R$^{31}$, the nitrogen to which it is attached and R$^{32}$ form a pyrrolidinyl, piperidinyl, N-methyl-piperazinyl, indolinyl or morpholinyl group, or a (C$_1$–C$_4$)alkoxycarbonyl-substituted pyrrolidinyl, piperidinyl, N-methylpiperazinyl, indolinyl or morpholinyl group;

Ar$^1$ is aryl or R$^{10}$-substituted aryl;

Ar$^2$ is aryl or R$^{11}$-substituted aryl;

Q is a bond or, with the 3-position ring carbon of the azetidinone, forms the spiro group

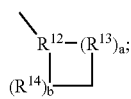

and

R[1] is selected from the group consisting of

—(CH$_2$)$_q$—, wherein q is 2–6, provided that when Q forms a spiro ring, q can also be zero or 1;

—(CH$_2$)$_e$-E-(CH$_2$)$_r$—, wherein E is —O—, —C(O)—, phenylene, —NR[22]— or —S(O)$_{0-2}$—, e is 0–5 and r is 0–5, provided that the sum of e and r is 1–6;

—(C$_2$-C$_6$)alkenylene-; and

—(CH$_2$)$_f$—V—(CH$_2$)$_g$—, wherein V is C$_3$-C$_6$ cycloalkylene, f is 1–5 and g is 0–5, provided that the sum of f and g is 1–6;

R[12] is

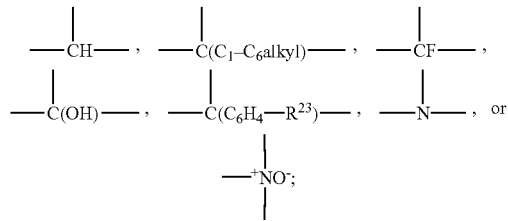

R[13] and R[14] are independently selected from the group consisting of —CH$_2$—, —CH(C$_1$-C$_6$ alkyl)-, —C(di-(C$_1$-C$_6$) alkyl), —CH=CH— and —C(C$_1$-C$_6$ alkyl)=CH—; or R[12] together with an adjacent R[13], or R[12] together with an adjacent R[14], form a —CH=CH— or a —CH=C(C$_1$-C$_6$ alkyl)- group;

a and b are independently 0, 1, 2 or 3, provided both are not zero;

provided that when R[13] is —CH=CH— or —C(C$_1$-C$_6$ alkyl)=CH—, a is 1;

provided that when R[14] is —CH=CH— or —C(C$_1$-C$_6$ alkyl)=CH—, b is 1;

provided that when a is 2 or 3, the R[13]'s can be the same or different; and provided that when b is 2 or 3, the R[14]'s can be the same or different;

and when Q is a bond, R[1] also can be:

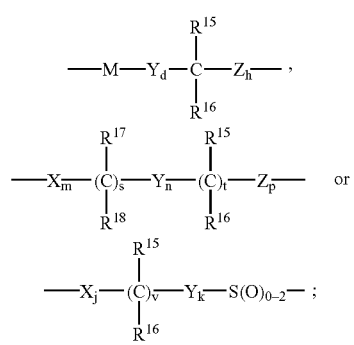

M is —O—, —S—, —S(O)— or —S(O)$_2$—;

X, Y and Z are independently selected from the group consisting of —CH$_2$—, —CH(C$_1$-C$_6$)alkyl- and —C(di-(C$_1$-C$_6$)alkyl);

R[10] and R[11] are independently selected from the group consisting of 1–3 substituents independently selected from the group consisting of (C$_1$-C$_6$)alkyl, —OR[19], —O(CO)R[19], —O(CO)OR[21], —O(CH$_2$)$_{1-5}$OR[19], —O(CO)NR[19]R[20], —NR[19]R[20], —NR[19](CO)R[20], —NR[19](CO)OR[21], —NR[19](CO)NR[20]R[25], —NR[19]SO$_2$R[21], —COOR[19], —CONR[19]R[20], —COR[19], —SO$_2$NR[19]R[20], S(O)$_{0-2}$R[21], —O(CH$_2$)$_{1-10}$—COOR[19], —O(CH$_2$)$_{1-10}$CONR[19]R[20], —(C$_1$-C$_6$ alkylene)-COOR[19], —CH=CH—COOR[19], —CF$_3$, —CN, —NO$_2$ and halogen;

R[15] and R[17] are independently selected from the group consisting of —OR[19], —O(CO)R[19], —O(CO)OR[21] and —O(CO)NR[19]R[20];

R[16] and R[18] are independently selected from the group consisting of H, (C$_1$-C$_6$)alkyl and aryl; or R[15] and R[16] together are =O, or R[17] and R[18] together are =O;

d is 1, 2 or 3;

h is 0, 1, 2, 3 or 4;

s is 0 or 1; t is 0 or 1; m, n and p are independently 0–4;

provided that at least one of s and t is 1, and the sum of m, n, p, s and t is 1–6;

provided that when p is 0 and t is 1, the sum of m, s and n is 1–5; and provided that when p is 0 and s is 1, the sum of m, t and n is 1–5;

v is 0 or, 1;

j and k are independently 1–5, provided that the sum of j, k and v is 1–5;

and when Q is a bond and R[1] is

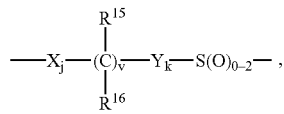

Ar[1] can also be pyridyl, isoxazolyl, furanyl, pyrrolyl, thienyl, imidazolyl, pyrazolyl, thiazolyl, pyrazinyl, pyrimidinyl or pyridazinyl;

R[19] and R[20] are independently selected from the group consisting of H, (C$_1$-C$_6$)alkyl, aryl and aryl-substituted (C$_1$-C$_6$)alkyl;

R[21] is (C$_1$-C$_6$)alkyl, aryl or R[24]-substituted aryl;

R[22] is H, (C$_1$-C$_6$)alkyl, aryl (C$_1$-C$_6$)alkyl, —C(O)R[19] or —COOR[19];

R[23] and R[24] are independently 1–3 groups independently selected from the group consisting of H, (C$_1$-C$_6$)alkyl, (C$_1$-C$_6$)alkoxy, —COOH, NO$_2$, —NR[19]R[20], —OH and halogeno; and R[25] is H, —OH or (C$_1$-C$_6$)alkoxy.

Ar[2] is preferably phenyl or R[11]-phenyl, especially (4-R[11])-substituted phenyl. Preferred definitions of R[11] are lower alkoxy, especially methoxy, and halogeno, especially fluoro.

Ar[1] is preferably phenyl or R[10]-substituted phenyl, especially (4-R[10])-substituted phenyl. Preferably R[10] is halogeno, and more preferably fluoro.

There are several preferred definitions for the —R[1]-Q-combination of variables:

Q is a bond and R[1] is lower alkylene, preferably propylene;

Q is a spiro group as defined above, wherein preferably $R^{13}$ and $R^{14}$ are each ethylene and $R^{12}$ is

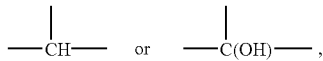

and $R^1$ is $—(CH_2)_q$ wherein q is 0–6;

Q is a bond and $R^1$ is

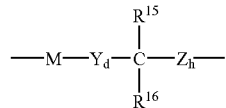

wherein the variables are chosen such that $R^1$ is $—O—CH_2—CH(OH)—$;

Q is a bond and $R^1$

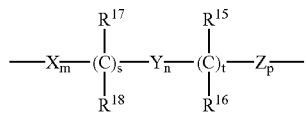

wherein the variables are chosen such that $R^1$ is $—CH(OH)—(CH_2)_2—$; and

Q is a bond and $R^1$ is

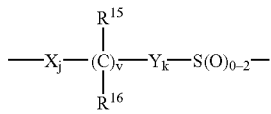

wherein the variables are chosen such that $R^1$ is $—CH(OH)—CH_2—S(O)_{0-2}—$.

A preferred compound of Formula (VIII) therefore, is one wherein G and $G^1$ are as defined above and in which the remaining variables have the following definitions:

$Ar^1$ is phenyl or $R^{10}$-substituted phenyl, wherein $R^{10}$ is halogeno;

$Ar^2$ is phenyl or $R^{11}$-phenyl, wherein $R^{11}$ is 1 to 3 substituents independently selected from the group consisting of $C_1$–$C_6$ alkoxy and halogeno;

Q is a bond and $R^1$ is lower alkylene; Q, with the 3-position ring carbon of the azetidinone, forms the group

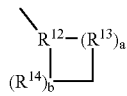

wherein preferably $R^{13}$ and $R^{14}$ are each ethylene and a and b are each 1, and wherein $R^{12}$ is $—CH—$ or $—C(OH)—$; Q is a bond and $R^1$ is $—O—CH_2—CH(OH)—$; Q is a bond and $R^1$ is $—CH(OH)—(CH_2)_2—$; or Q is a bond and $R^1$ is $—CH(OH)—CH_2—S(O)_{0-2}—$.

Preferred variables for G and $G^1$ groups of the formulae are as follows:

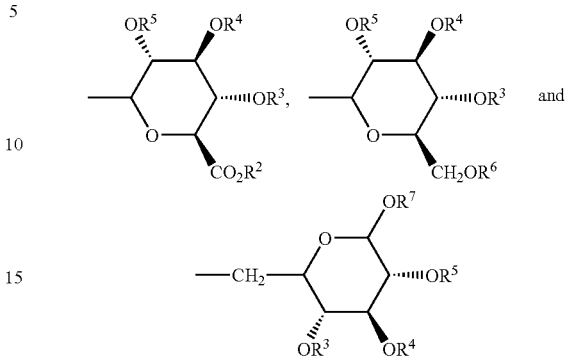

$R^2$, $R^3$, $R^4$, $R^5$, $R^6$ and $R^7$ are independently selected from the group consisting of H, $(C_1$–$C_6)$alkyl, benzyl and acetyl.

Preferred variables for group G or $G^1$ of the formula:

are as follows:

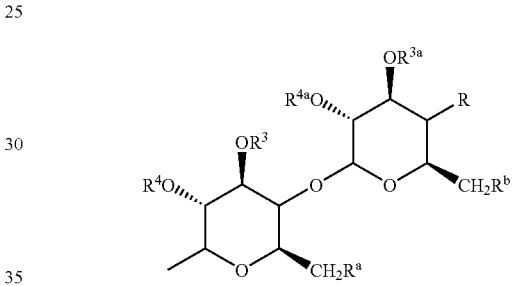

$R^3$, $R^{3a}$, $R^4$ and $R^{4a}$ are selected from the group consisting of H, $(C_1$–$C_6)$alkyl, benzyl and acetyl;

R, $R^a$ and $R^b$ are independently selected from the group consisting of H, $—OH$, halogeno, $—NH_2$, azido, $(C_1$–$C_6)$alkoxy$(C_1$–$C_6)$alkoxy and $—W—R^{30}$, wherein W is $—O—C(O)—$ or $—O—C(O)—NR^{31}—$, $R^{31}$ is H and $R^{30}$ is $(C_1$–$C_6)$alkyl, $—C(O)—(C_1$–$C_4)$alkoxy-$(C_1$–$C_6)$alkyl, T, T-$(C_1$–$C_6)$alkyl, or T or T-$(C_1$–$C_6)$alkyl wherein T is substituted by one or two halogeno or $(C_1$–$C_6)$ alkyl groups.

Preferred $R^{30}$ substituents are selected from the group consisting of: 2-fluorophenyl, 2,4-difluoro-phenyl, 2,6-dichlorophenyl, 2-methylphenyl, 2-thienylmethyl, 2-methoxy-carbonylethyl, thiazol-2-yl-methyl, 2-furyl, 2-methoxycarbonylbutyl and phenyl.

Preferred combinations of R, $R^a$ and $R^b$ are as follows:

1) R, $R^a$ and $R^b$ are independently $—OH$ or $—O—C(O)—NH—R^{30}$, especially to wherein $R^a$ is $—OH$ and R and $R^b$ are $—O—C(O)—NH—R^{30}$ and $R^{30}$ is selected from the preferred substituents identified above, or wherein R and $R^a$ are each $—OH$ and $R^b$ is $—O—C(O)—NH—R^{30}$ wherein $R^{30}$ is 2-fluorophenyl, 2,4-difluorophenyl, 2,6-dichlorophenyl;

2) $R^a$ is $—OH$, halogeno, azido or $(C_1$–$C_6)$-alkoxy$(C_1$–$C_6)$alkoxy, $R^b$ is H, halogeno, azido or $(C_1$–$C_6)$ alkoxy$(C_1$–$C_6)$-alkoxy, and R is $—O—C(O)—NH—R^{30}$, especially compounds wherein $R^a$ is $—OH$, $R^b$ is H and $R^{30}$ is 2-fluorophenyl;

3) R, $R^a$ and $R^b$ are independently $—OH$ or $—O—C(O)—R^{30}$ and $R^{30}$ is $(C_1$–$C_6)$alkyl, T, or T substituted by one or two halogeno or $(C_1-C_6)$alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional classes of preferred compounds are those wherein the $C^{1'}$ anomeric oxy is beta, wherein the $C^{2'}$ anomeric oxy is beta, and wherein the R group is alpha. G and $G^1$ are preferably selected from:

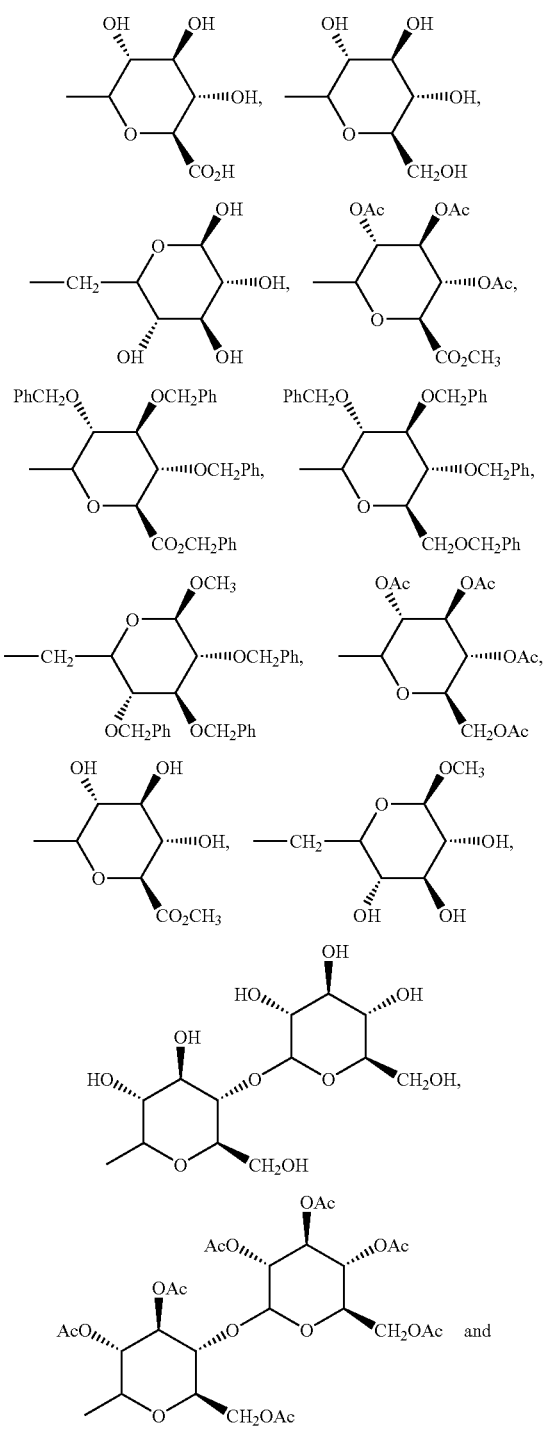

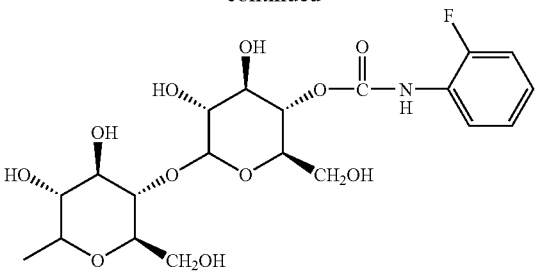

wherein Ac is acetyl and Ph is phenyl.

Preferably, $R^{26}$ is H or OH, more preferably H. The —O-G substituent is preferably in the 4-position of the phenyl ring to which it is attached.

In another embodiment, sterol or 5α-stanol absorption inhibitors useful in the compositions and methods of the present invention are represented by Formula (IX) below:

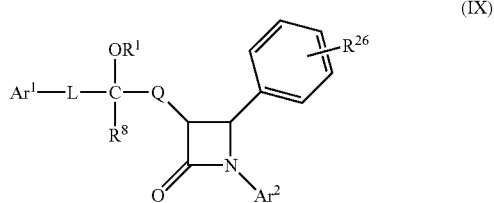

(IX)

or a pharmaceutically acceptable salt or solvate thereof, wherein in Formula (IX):

$R^1$ is selected from the group consisting of H, G, $G^1$, $G^2$, —$SO_3H$ and —$PO_3H$;

G is selected from the group consisting of: H,

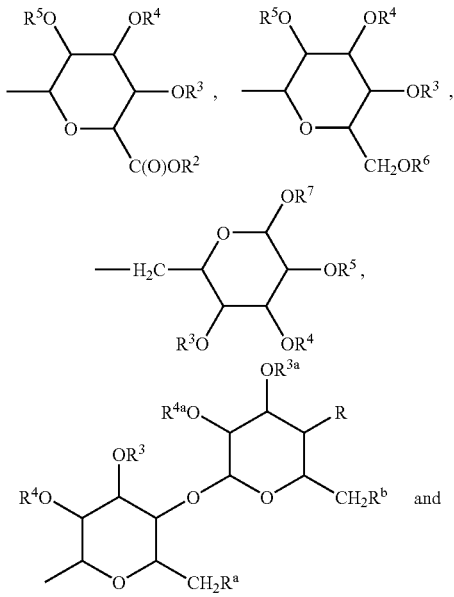

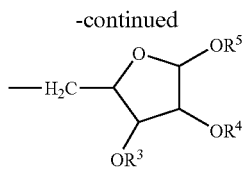

(sugar derivatives)

wherein R, $R^a$ and $R^b$ are each independently selected from the group consisting of H, —OH, halo, —NH$_2$, azido, $(C_1-C_6)$alkoxy$(C_1-C_6)$alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are each independently selected from the group consisting of H, $(C_1-C_6)$alkyl, acetyl, aryl and aryl$(C_1-C_6)$alkyl;

$R^3$, $R^4$, $R^5$, $R^7$, $R^{3a}$ and $R^{4a}$ are each independently selected from the group consisting of H, $(C_1-C_6)$alkyl, acetyl, aryl$(C_1-C_6)$alkyl, —C(O)$(C_1-C_6)$alkyl and —C(O)aryl;

$R^{30}$ is independently selected from the group consisting of $R^{32}$-substituted T, $R^{32}$-substituted-T-$(C_1-C_6)$alkyl, $R^{32}$-substituted-$(C_2-C_4)$alkenyl, $R^{32}$-substituted-$(C_1-C_6)$alkyl, $R^{32}$-substituted-$(C_{3-C7})$cycloalkyl and $R^{32}$-substituted-$(C_3-C_7)$cycloalkyl $(C_1-C_6)$alkyl;

$R^{31}$ is independently selected from the group consisting of H and $(C_1-C_4)$alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1–3 substituents which are each independently selected from the group consisting of H, halo, $(C_1-C_4)$alkyl, —OH, phenoxy, —CF$_3$, —NO$_2$, $(C_{1-C4})$alkoxy, methylenedioxy, oxo, $(C_{1-C4})$alkylsulfanyl, $(C_{1-C4})$alkylsulfinyl, $(C_1-C_4)$alkylsulfonyl, —N(CH$_3$)$_2$, —C(O)—NH$(C_1-C_4)$alkyl, —C(O)—N$((C_1-C_4)$alkyl)$_2$, —C(O)—$(C_1-C_4)$alkyl, —C(O)—$(C_{1-C4})$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a $(C_1-C_4)$alkoxycarbonyl-substituted pyrrolidinyl, piperidinyl, N-methylpiperazinyl, indolinyl or morpholinyl group;

$G^1$ is represented by the structure:

wherein $R^{33}$ is independently selected from the group consisting of unsubstituted alkyl, $R^{34}$-substituted alkyl, $(R^{35})(R^{36})$alkyl-,

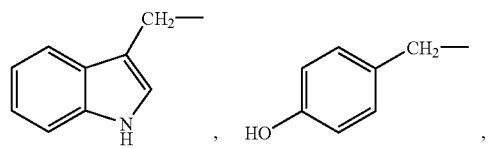

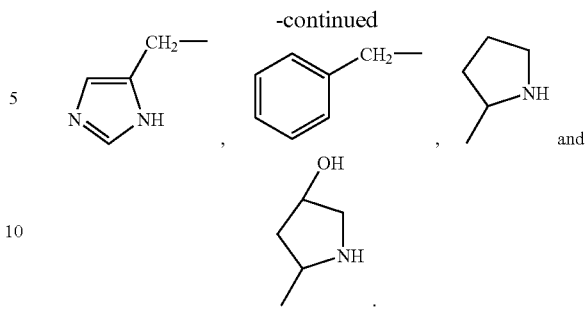

$R^{34}$ is one to three substituents, each $R^{34}$ being independently selected from the group consisting of HOOC—, HS—, (CH$_3$)S—, H$_2$N—, (NH$_2$)(NH)C(NH)—, (NH$_2$)C(O)— and HOOCCH(NH$_3^+$)CH$_2$SS—;

$R^{35}$ is independently selected from the group consisting of H and NH$_2$—;

$R^{36}$ is independently selected from the group consisting of H, unsubstituted alkyl, $R^{34}$-substituted alkyl, unsubstituted cycloalkyl and $R^{34}$-substituted cycloalkyl;

$G^2$ is represented by the structure:

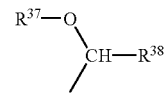

wherein $R^{37}$ and $R^{38}$ are each independently selected from the group consisting of $(C_1-C_6)$alkyl and aryl;

$R^{26}$ is one to five substituents, each $R^{26}$ being independently selected from the group consisting of:
a) H;
b) —OH;
c) —OCH$_3$;
d) fluorine;
e) chlorine;
f) —O-G;
g) —O-G$^1$;
h) —O-G$^2$;
i) —SO$_3$H; and
j) —PO$_3$H;

provided that when $R^1$ is H, $R^{26}$ is not H, —OH, —OCH$_3$ or —O-G;

Ar$^1$ is aryl, $R^{10}$-substituted aryl, heteroaryl or $R^{10}$-substituted heteroaryl;

Ar$^2$ is aryl, $R^{11}$-substituted aryl, heteroaryl or $R^{11}$-substituted heteroaryl;

L is selected from the group consisting of:
a) a covalent bond;
b) —(CH$_2$)$_q$—, wherein q is 1–6;
c) —(CH$_2$)$_e$-E-(CH$_2$)$_r$—, wherein E is —O—, —C(O)—, phenylene, —NR$^{22}$— or —S(O)$_{0-2}$—, e is 0–5 and r is 0–5, provided that the sum of e and r is 1–6;
d) —(C$_2$–C$_6$)alkenylene-;
e) —(CH$_2$)$_f$—V—(CH$_2$)$_g$—, wherein V is C$_3$–C$_6$cycloalkylene, f is 1–5 and g is 0–5, provided that the sum of f and g is 1–6; and
f)

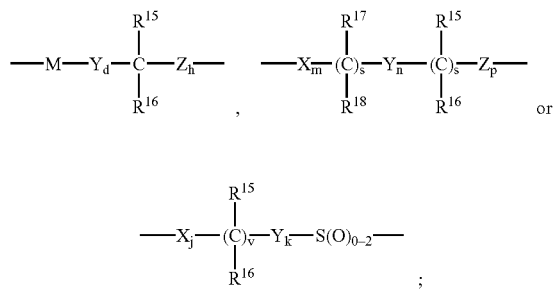

wherein M is —O—, —S—, —S(O)— or —S(O)$_2$—;

X, Y and Z are each independently selected from the group consisting of —CH$_2$—, —CH(C$_1$–C$_6$)alkyl- and —C(di-(C$_1$–C$_6$)alkyl)-;

R$^8$ is selected from the group consisting of H and alkyl;

R$^{10}$ and R$^{11}$ are each independently selected from the group consisting of 1–3 substituents which are each independently selected from the group consisting of (C$_1$–C$_6$) alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_{2l}$)$_{1-10}$—COOR$^{19}$, —O(CH$_2$)$_{1-10}$CONR$^{19}$R$^{20}$, —(C$_1$–C$_6$ alkylene)-COOR$^{19}$, —CH=CH—COOR$^{19}$, —CF$_3$, —CN, —NO$_2$ and halo;

R$^{15}$ and R$^{17}$ are each independently selected from the group consisting of —OR$^{19}$, —OC(O)R$^{19}$, —OC(O)OR$^{21}$, —OC(O)NR$^{19}$R$^{20}$;

R$^{16}$ and R$^{18}$ are each independently selected from the group consisting of H, (C$_1$–C$_6$)alkyl and aryl;

or R$^{15}$ and R$^{16}$ together are =O, or R$^{17}$ and R$^{18}$ together are =O;

d is 1, 2 or 3;

h is 0, 1, 2, 3 or 4;

s is 0 or 1;

t is 0 or 1;

m, n and p are each independently selected from 0–4; provided that at least one of s and t is 1, and the sum of m, n, p, s and t is 1–6; provided that when p is 0 and t is 1, the sum of m, n and p is 1–5; and provided that when p is 0 and s is 1, the sum of m, t and n is 1–5;

v is 0 or 1;

j and k are each independently 1–5, provided that the sum of j, k and v is 1–5;

Q is a bond, —(CH$_2$)$_q$—, wherein q is 1–6, or, with the 3-position ring carbon of the azetidinone, forms the spiro group

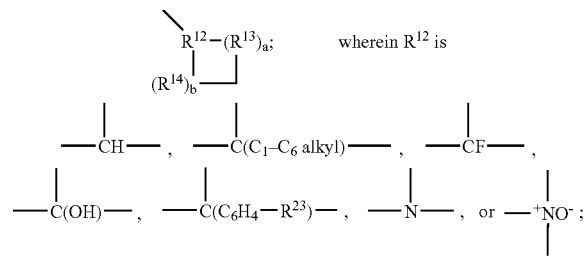

wherein R$^{12}$ is

R$^{13}$ and R$^{14}$ are each independently selected from the group consisting of —CH$_2$—, —CH(C$_1$–C$_6$ alkyl)-, —C(di-(C$_1$–C$_6$) alkyl), —CH=CH— and —C(C$_1$–C$_6$ alkyl)=CH—; or R$^{12}$ together with an adjacent R$^{13}$, or R$^{12}$ together with an adjacent R$^{14}$, form a —CH=CH— or a —CH=C(C$_1$–C$_6$ alkyl)- group;

a and b are each independently 0, 1, 2 or 3, provided both are not zero; provided that when R$^{13}$ is —CH=CH— or —C(C$_1$–C$_6$ alkyl)=CH—, a is 1; provided that when R$^{14}$ is —CH=CH— or —C(C$_{1-C6}$ alkyl)=CH—, b is 1; provided that when a is 2 or 3, the R$^{13}$'s can be the same or different; and provided that when b is 2 or 3, the R$^{14}$'s can be the same or different;

and when Q is a bond and L is

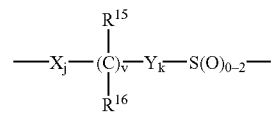

then Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

R$^{19}$ and R$^{20}$ are each independently selected from the group consisting of H, (C$_1$–C$_6$)alkyl, aryl and aryl-substituted (C$_1$–C$_6$)alkyl;

R$^{21}$ is (C$_1$–C$_6$)alkyl, aryl or R$^{24}$-substituted aryl;

R$^{22}$ is H, (C$_1$–C$_6$)alkyl, aryl (C$_1$–C$_6$)alkyl, —C(O)R$^{19}$ or —COOR$^{19}$;

R$^{23}$ and R$^{24}$ are each independently selected from the group consisting of 1–3 substituents which are each independently selected from the group consisting of H, (C$_1$–C$_6$) alkyl, (C$_1$–C$_6$)alkoxy, —COOH, NO$_2$, —NR$^{19}$R$^{20}$, —OH and halo; and R$^{25}$ is H, —OH or (C$_1$–C$_6$)alkoxy.

Examples of compounds of Formula (IX) which are useful in the methods and combinations of the present invention and methods for making such compounds are disclosed in U.S. patent application Ser. No. 10/166,942, filed Jun. 11, 2002, incorporated herein by reference. An example of a useful compound of this invention is one represented by the formula X:

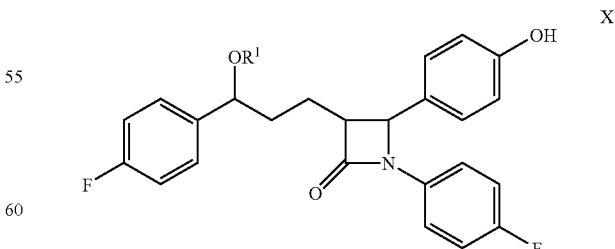

wherein R$^1$ is defined as above.

A more preferred compound is one represented by formula XI:

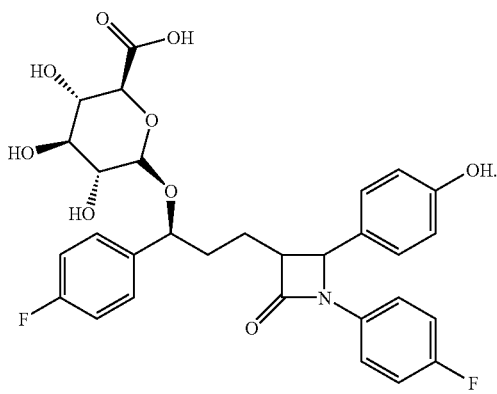

(XI)

Another useful compound is represented by Formula XII:

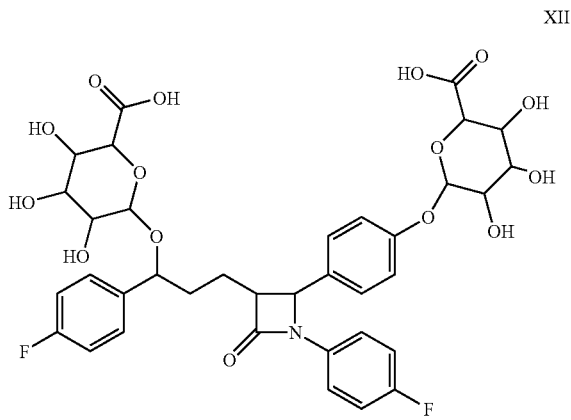

XII

The compounds of Formulae I–XII can be prepared by known methods, including the methods discussed above and, for example, WO 93/02048 describes the preparation of compounds wherein —$R^1$-Q- is alkylene, alkenylene or alkylene interrupted by a hetero atom, phenylene or cycloalkylene; WO 94/17038 describes the preparation of compounds wherein Q is a spirocyclic group; WO 95/08532 describes the preparation of compounds wherein —$R^1$-Q- is a hydroxy-substituted alkylene group; PCT/US95/03196 describes compounds wherein —$R^1$-Q- is a hydroxy-substituted alkylene attached to the $Ar^1$ moiety through an —O— or $S(O)_{0-2}$— group; and U.S. Ser. No. 08/463,619, filed Jun. 5, 1995, describes the preparation of compounds wherein —$R^1$-Q- is a hydroxy-substituted alkylene group attached the azetidinone ring by a —$S(O)_{0-2}$— group.

The daily dose of the sterol or 5α-stanol absorption inhibitor(s) administered to the subject can range from about 0.1 to about 1000 mg per day, preferably about 0.25 to about 50 mg/day, and more preferably about 10 mg per day, given in a single dose or 2–4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

The methods, compositions, and therapeutic combinations of the present invention may also include co-administering an effective amount of another therapeutic composition. These therapeutic compositions may include HMG-CoA reductase inhibitors, peroxisome proliferator-activated receptor activators, obesity medications, probucol or derivatives thereof, low-density lipoprotein receptor activators, Omega 3 fatty acids, nicotinic acid or a derivative thereof, Acyl CoA: cholesterol O-acyl transferase inhibitors, natural water solid fibers, plant sterols, plant stanols, fatty acid esters of plant stanols, antioxidants, vitamins, hormone replacements, obesity control agents, diabetes control agents, blood modifiers, cardiovascular agents, other therapeutic agents described below, and combinations thereof.

Also useful in the present invention are compositions or therapeutic combinations that further comprise at least one (one or more) activators for peroxisome proliferator-activated receptors (PPAR). The activators act as agonists for the peroxisome proliferator-activated receptors. Three subtypes of PPAR have been identified, and these are designated as peroxisome proliferator-activated receptor alpha (PPARα), peroxisome proliferator-activated receptor gamma (PPARγ) and peroxisome proliferator-activated receptor delta (PPARδ). It should be noted that PPARδ is also referred to in the literature as PPARβ and as NUC1, and each of these names refers to the same receptor.

PPARα regulates the metabolism of lipids. PPARα is activated by fibrates and a number of medium and long-chain fatty acids, and it is involved in stimulating β-oxidation of fatty acids. The PPARγ receptor subtypes are involved in activating the program of adipocyte differentiation and are not involved in stimulating peroxisome proliferation in the liver. PPARδ has been identified as being useful in increasing high density lipoprotein (HDL) levels in humans. See, e.g., WO 97/28149.

PPARα activator compounds are useful for, among other things, lowering triglycerides, moderately lowering LDL levels and increasing HDL levels. Useful examples of PPARα activators include fibrates.

Non-limiting examples of suitable fibric acid derivatives ("fibrates") include clofibrate (such as ethyl 2-(p-chlorophenoxy)-2-methyl-propionate, for example ATROMID-S® Capsules which are commercially available from Wyeth-Ayerst); gemfibrozil (such as 5-(2,5-dimethylphenoxy)-2,2-dimethylpentanoic acid, for example LOPID® tablets which are commercially available from Parke Davis); ciprofibrate (C.A.S. Registry No. 52214-84-3, see U.S. Pat. No. 3,948,973 which is incorporated herein by reference); bezafibrate (C.A.S. Registry No. 41859-67-0, see U.S. Pat. No.3,781,328 which is incorporated herein by reference); clinofibrate (C.A.S. Registry No.30299-08-2, see U.S. Pat. No. 3,716,583 which is incorporated herein by reference); binifibrate (C.A.S. Registry No. 69047-39-8, see BE 884722 which is incorporated herein by reference); lifibrol (C.A.S. Registry No. 96609-16-4); fenofibrate (such as TRICOR® micronized fenofibrate (2-[4-(4-chlorobenzoyl) phenoxy]-2-methyl-propanoic acid, 1-methylethyl ester) which is commercially available from Abbott Laboratories or LIPANTHYL® micronized fenofibrate which is commercially available from Labortoire Founier, France) and mixtures thereof. These compounds can be used in a variety of forms, including but not limited to acid form, salt form, racemates, enantiomers, zwitterions and tautomers.

Other examples of PPARα activators useful in the practice of the present invention include suitable fluorophenyl compounds as disclosed in U.S. Pat. No. 6,028,109 which is incorporated herein by reference; certain substituted phenylpropionic compounds as disclosed in WO 00/75103 which is incorporated herein by reference; and PPARα activator compounds as disclosed in WO 98/43081 which is incorporated herein by reference.

Non-limiting examples of suitable PPARγ activators include derivatives of glitazones or thiazolidinediones, such as, troglitazone (such as REZULIN® troglitazone (-5-[[4-[3,4-dihydro-6-hydroxy-2,5,7,8-tetramethyl-2H-1 -benzopyran-2-yl)methoxy]phenyl]methyl]-2,4-thiazolidinedione) commercially available from Parke-Davis); rosiglitazone (such as AVANDIA® rosiglitazone maleate (-5-[[4-[2-(methyl-2-pyridinylamino)ethoxy]phenyl]methyl]-2,4-thiazolidinedione, -2-butenedioate) commercially available from SmithKline Beecham) and pioglitazone (such as ACTOS™ pioglitazone hydrochloride (5-[[4-[2-(5-ethyl-2-pyridinyl)ethoxy]phenyl]methyl]-2,4-]thiazolidinedione monohydrochloride) commercially available from Takeda Pharmaceuticals). Other useful thiazolidinediones include ciglitazone, englitazone, darglitazone and BRL 49653 as disclosed in WO 98/05331 which is incorporated herein by reference; PPARγ activator compounds disclosed in WO 00/76488 which is incorporated herein by reference; and PPARy activator compounds disclosed in U.S. Pat. No. 5,994,554 which is incorporated herein by reference.

Other useful PPARγ activator compounds include certain acetylphenols as disclosed in U.S. Pat. No. 5,859,051 which is incorporated herein by reference; certain quinoline phenyl compounds as disclosed in WO 99/20275 which is incorporated herein by reference; aryl compounds as disclosed by WO 99/38845 which is incorporated herein by reference; certain 1,4-disubstituted phenyl compounds as disclosed in WO 00/63161; certain aryl compounds as disclosed in WO 01/00579 which is incorporated herein by reference; benzoic acid compounds as disclosed in WO 01/12612 & WO 01/12187 which are incorporated herein by reference; and substituted 4-hydroxy-phenylalconic acid compounds as disclosed in WO 97/31907 which is incorporated herein by reference.

PPARδ compounds are useful for, among other things, lowering triglyceride levels or raising HDL levels. Non-limiting examples of PPARδ activators include suitable thiazole and oxazole derivatives, such as C.A.S. Registry No. 317318-32-4, as disclosed in WO 01/00603 which is incorporated herein by reference); certain fluoro, chloro or thio phenoxy phenylacetic acids as disclosed in WO 97/28149 which is incorporated herein by reference; suitable non-β-oxidizable fatty acid analogues as disclosed in U.S. Pat. No. 5,093,365 which is incorporated herein by reference; and PPARδ compounds as disclosed in WO 99/04815 which is incorporated herein by reference.

Moreover, compounds that have multiple functionality for activating various combinations of PPARα, PPARγ and PPARδ are also useful with the practice of the present invention. Non-limiting examples include certain substituted aryl compounds as disclosed in U.S. Pat. No. 6,248,781; WO 00/23416; WO 00/23415; WO 00/23425; WO 00/23445; WO 00/23451; and WO 00/63153, all of which are incorporated herein by reference, are described as being useful PPARα and/or PPARγ activator compounds. Other non-limiting examples of useful PPARα and/or PPARγ activator compounds include activator compounds as disclosed in WO 97/25042 which is incorporated herein by reference; activator compounds as disclosed in WO 00/63190 which is incorporated herein by reference; activator compounds as disclosed in WO 01/21181 which is incorporated herein by reference; biaryl-oxa(thia)zole compounds as disclosed in WO 01/16120 which is incorporated herein by reference; compounds as disclosed in WO 00/63196 and WO 00/63209 which are incorporated herein by reference; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G which are incorporated herein by reference; GW2331 or (2-(4-[difluorophenyl]-1heptylureido)ethyl]phenoxy)-2-methylbutyric compounds as disclosed in WO 98/05331 which is incorporated herein by reference; aryl compounds as disclosed in U.S. Pat. No. 6,166,049 which is incorporated herein by reference; oxazole compounds as disclosed in WO 01/17994 which is. incorporated herein by reference; and dithiolane compounds as disclosed in WO 01/25225 and WO 01/25226 which are incorporated herein by reference.

Other useful PPAR activator compounds include substituted benzylthiazolidine-2,4-dione compounds as disclosed in WO 01/14349, WO 01/14350 and WO/01/04351 which are incorporated herein by reference; mercaptocarboxylic compounds as disclosed in WO 00/50392 which is incorporated herein by reference; ascofuranone compounds as disclosed in WO 00/53563 which is incorporated herein by reference; carboxylic compounds as disclosed in WO 99/46232 which is incorporated herein by reference; compounds as disclosed in WO 99/12534 which is incorporated herein by reference; benzene compounds as disclosed in WO 99/15520 which is incorporated herein by reference; o-anisamide compounds as disclosed in WO 01/21578 which is incorporated herein by reference; and PPAR activator compounds as disclosed in WO 01/40192 which is incorporated herein by reference.

The peroxisome proliferator-activated receptor(s) activator(s) are administered in a therapeutically effective amount to treat the specified condition, for example in a daily dose preferably ranging from about 50 to about 3000 mg per day, and more preferably about 50 to about 2000 mg per day, given in a single dose or 2–4 divided doses. The exact dose, however, is determined by the attending clinician and is dependent on such factors as the potency of the compound administered, the age, weight, condition and response of the patient.

The compositions or therapeutic combinations of the present invention can further comprise one or more pharmacological or therapeutic agents or drugs such as cholesterol biosynthesis inhibitors and/or lipid-lowering agents discussed below.

Non-limiting examples of cholesterol biosynthesis inhibitors for use in the compositions, therapeutic combinations and methods of the present invention include competitive inhibitors of HMG CoA reductase, the rate-limiting step in cholesterol biosynthesis, squalene synthase inhibitors, squalene epoxidase inhibitors and mixtures thereof. Non-limiting examples of suitable HMG CoA reductase inhibitors include statins such as lovastatin (for example MEVACOR® which is available from Merck & Co.), pravastatin (for example PRAVACHOL® which is available from Bristol Meyers Squibb), fluvastatin, simvastatin (for example ZOCOR® which is available from Merck & Co.), atorvastatin, cerivastatin, CI-981, rivastatin (sodium 7-(4-fluorophenyl)-2,6-diisopropyl-5-methoxymethylpyridin-3-yl )-3,5-dihydroxy-6-heptanoate), rosuvastatin and pitavastatin (such as NK-104 of Negma Kowa of Japan); HMG CoA synthetase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy] benzene-methanamine hydrochloride) and other sterol biosynthesis inhibitors such as DMP-565. Preferred HMG CoA reductase inhibitors include lovastatin, pravastatin and simvastatin. The most preferred HMG CoA reductase inhibitor is simvastatin.

Generally, a total daily dosage of cholesterol biosynthesis inhibitor(s) can range from about 0.1 to about 160 mg per day, and preferably about 0.2 to about 80 mg/day in single or 2–3 divided doses.

The compositions, therapeutic combinations or methods of the present invention can further comprise one or more bile acid sequestrants. Bile acid sequestrants bind bile acids in the intestine, interrupting the enterohepatic circulation of bile acids and causing an increase in the faecal excretion of steroids. Use of bile acid sequestrants is desirable because of their non-systemic mode of action. Bile acid sequestrants can lower intrahepatic cholesterol and promote the synthesis of apo B/E (LDL) receptors which bind LDL from plasma to further reduce cholesterol levels in the blood.

Non-limiting examples of suitable bile acid sequestrants include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

Generally, a total daily dosage of bile acid sequestrant(s) can range from about 1 to about 50 grams per day, and preferably about 2 to about 16 grams per day in single or 2–4 divided doses.

The compositions or treatments of the present invention can further comprise one or more ileal bile acid transport ("IBAT") inhibitors (or apical sodium co-dependent bile acid transport ("ASBT") inhibitors) coadministered with or in combination with the peroxisome proliferator-activated receptor activator(s) and sterol absorption inhibitor(s) discussed above. The IBAT inhibitors can inhibit bile acid transport to reduce LDL cholesterol levels. Non-limiting examples of suitable IBAT inhibitors include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference.

Generally, a total daily dosage of IBAT inhibitor(s) can range from about 0.01 to about 1000 mg/day, and preferably about 0.1 to about 50 mg/day in single or 2–4 divided doses.

The compositions or treatments of the present invention can further comprise nicotinic acid (niacin) and/or derivatives thereof. As used herein, "nicotinic acid derivative" means a compound comprising a pyridine-3-carboxylate structure or a pyrazine-2-carboxylate structure, including acid forms, salts, esters, zwitterions and tautomers, where available. Examples of nicotinic acid derivatives include niceritrol, nicofuranose and acipimox (5-methyl pyrazine-2-carboxylic acid 4-oxide). Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos.

Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

The compositions or treatments of the present invention can further comprise one or more AcylCoA:Cholesterol O-acyltransferase ("ACAT") Inhibitors, which can reduce VLDL levels, coadministered with or in combination with the peroxisome proliferator-activated receptor activator(s) and sterol absorption inhibitor(s) discussed above. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors include avasimibe ([[2,4,6-tris(1-methylethyl)phenyl]acetyl]sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea). See P. Chang et al., "Current, New and Future Treatments in Dyslipidaemia and Atherosclerosis", *Drugs* 2000 July;60(1); 55–93, which is incorporated by reference herein.

Generally, a total daily dosage of ACAT inhibitor(s) can range from about 0.1 to about 1000 mg/day in single or 2–4 divided doses.

The compositions or treatments of the present invention can further comprise one or more Cholesteryl Ester Transfer Protein ("CETP") Inhibitors coadministered with or in combination with the peroxisome proliferator-activated receptor activator(s) and sterol absorption inhibitor(s) discussed above. CETP is responsible for the exchange or transfer of cholesteryl ester carrying HDL and triglycerides in VLDL.

Non-limiting examples of suitable CETP inhibitors are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be coadministered with or in combination with the peroxisome proliferator-activated receptor(s) activator and sterol absorption inhibitor(s) discussed above.

Generally, a total daily dosage of CETP inhibitor(s) can range from about 0.01 to about 1000 mg/day, and preferably about 0.5 to about 20 mg/kg body weight/day in single or divided doses.

The compositions or treatments of the present invention can further comprise probucol or derivatives thereof (such as AGI-1067 and other derivatives disclosed in U.S. Pat. Nos. 6,121,319 and 6,147,250), which can reduce LDL levels, coadministered with or in combination with the peroxisome proliferator-activated receptor activator(s) and sterol absorption inhibitor(s) discussed above.

Generally, a total daily dosage of probucol or derivatives thereof can range from about 10 to about 2000 mg/day, and preferably about 500 to about 1500 mg/day in single or 2–4 divided doses.

The compositions or treatments of the present invention can further comprise low-density lipoprotein (LDL) receptor activators, coadministered with or in combination with the peroxisome proliferator-activated receptor activator(s) and sterol absorption inhibitor(s) discussed above. Non-limiting examples of suitable LDL-receptor activators include HOE-402, an imidazolidinyl-pyrimidine derivative that directly stimulates LDL receptor activity. See M. Hueftinger et al., "Hypolipidemic activity of HOE-402 is Mediated by Stimulation of the LDL Receptor Pathway", Arterioscler. Thromb. 1993; 13:1005–12.

Generally, a total daily dosage of LDL receptor activator(s) can range from about 1 to about 1000 mg/day in single or 2–4 divided doses.

The compositions or treatments of the present invention can further comprise fish oil, which contains Omega 3 fatty acids (3-PUFA), which can reduce VLDL and triglyceride levels, coadministered with or in combination with the peroxisome proliferator-activated receptor activator(s) and sterol absorption inhibitor(s) discussed above. Generally, a total daily dosage of fish oil or Omega 3 fatty acids can range from about 1 to about 30 grams per day in single or 2–4 divided doses.

The compositions or treatments of the present invention can further comprise natural water soluble fibers, such as psyllium, guar, oat and pectin, which can reduce cholesterol levels. Generally, a total daily dosage of natural water soluble fibers can range from about 0.1 to about 10 grams per day in single or 2–4 divided doses.

The compositions or treatments of the present invention can further comprise plant sterols, plant stanols and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day in single or 2–4 divided doses.

The compositions or treatments of the present invention can further comprise antioxidants, such as probucol, tocopherol, ascorbic acid, β-carotene and selenium, or vitamins such as vitamin $B_6$ or vitamin $B_{12}$. Generally, a total daily dosage of antioxidants or vitamins can range from about 0.05 to about 10 grams per day in single or 2–4 divided doses.

The compositions or treatments of the present invention can further comprise monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E. Generally, a total daily dosage of these agents can range from about 0.01 to about 1000 mg/day in single or 2–4 divided doses.

The present invention also provides a composition or therapeutic combination comprising (a) at least one Acyl-CoA:Cholesterol O-acyltransferase Inhibitor and (b) at least one substituted azetidinone compound or substituted β-lactam compound or a pharmaceutically acceptable salt thereof or a prodrug thereof.

Also useful with the present invention are compositions or therapeutic combinations that further comprise hormone replacement agents and compositions. Useful hormone agents and compositions include androgens, estrogens, progestins, their pharmaceutically acceptable salts and derivatives. Combinations of these agents and compositions also are useful.

The dosage of androgen and estrogen combinations vary, desirably from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone (17-hydroxy-17-methyl-, (17B)- androst-4-en-3-one) available from Solvay Pharmaceuticals, Inc., Marietta, Ga., under the tradename ESTRATEST.

Estrogens and estrogen combinations may vary in dosage from about 0.01 mg up to 8 mg, desirably from about 0.3 mg to about 3.0 mg. Examples of useful estrogens and estrogen combinations include:

(a) the blend of nine (9) synthetic estrogenic substances including sodium estrone sulfate, sodium equilin sulfate, sodium 17α-dihydroequilin sulfate, sodium 17α-estradiol sulfate, sodium 17β-dihydroequilin sulfate, sodium 17α-dihydroequilenin sulfate, sodium 17β-dihydroequilenin sulfate, sodium equilenin sulfate and sodium 17β-estradiol sulfate; available from Duramed Pharmaceuticals, Inc., Cincinnati, Ohio, under the tradename CENESTIN;

(b) ethinyl estradiol (19-nor-17α-pregna-1,3,5(10)-trien-20-yne-3,17-diol; available by Schering Plough Corporation, Kenilworth, N.J., under the tradename ESTINYL;

(c) esterified estrogen combinations such as sodium estrone sulfate and sodium equilin sulfate; available from Solvay under the tradename ESTRATAB and from Monarch Pharmaceuticals, Bristol, Tenn., under the tradename MENEST;

(d) estropipate (piperazine estra-1,3,5(10)-trien-17-one, 3-(sulfooxy)-estrone sulfate); available from Pharmacia & Upjohn, Peapack, N.J., under the tradename OGEN and from Women First Health Care, Inc., San Diego, Calif., under the tradename ORTHO-EST; and (e) conjugated estrogens (17α-dihydroequilin, 17α-estradiol, and 17β-dihydroequilin); available from Wyeth-Ayerst Pharmaceuticals, Philadelphia, Pa., under the tradename PREMARIN.

Progestins and estrogens may also be administered with a variety of dosages, generally from about 0.05 to about 2.0 mg progestin and about 0.001 mg to about 2 mg estrogen, desirably from about 0.1 mg to about 1 mg progestin and about 0.01 mg to about 0.5 mg estrogen. Examples of progestin and estrogen combinations that may vary in dosage and regimen include:

(a) the combination of estradiol (estra-1,3,5(10)-triene-3, 17β-diol hemihydrate) and norethindrone (17β-acetoxy-19-nor-17α-pregn-4-en-20-yn-3-one); which is available from Pharmacia & Upjohn, Peapack, N.J., under the tradename ACTIVELLA;

(b) the combination of levonorgestrel (d(−)-13β-ethyl-17α-ethinyl-17β-hydroxygon-4-en-3-one) and ethinyl estradiol; available from Wyeth-Ayerst under the tradename ALESSE, from Watson Laboratories, Inc., Corona, Calif., under the tradenames LEVORA and TRIVORA, Monarch Pharmaceuticals, under the tradename NORDETTE, and from Wyeth-Ayerst under the tradename TRIPHASIL;

(c) the combination of ethynodiol diacetate (19-nor-17α-pregn-4-en-20-yne-3β, 17-diol diacetate) and ethinyl estradiol; available from G.D. Searle & Co., Chicago, Ill., under the tradename DEMULEN and from Watson under the tradename ZOVIA;

(d) the combination of desogestrel (13-ethyl-11-methylene-18,19-dinor-17α-pregn-4-en-20-yn-17-ol) and ethinyl estradiol; available from Organon under the tradenames DESOGEN and MIRCETTE, and from Ortho-McNeil Pharmaceutical, Raritan, N.J., under the tradename ORTHO-CEPT;

(e) the combination of norethindrone and ethinyl estradiol; available from Parke-Davis, Morris Plains, N.J., under the tradenames ESTROSTEP and FEMHRT, from Watson under the tradenames MICROGESTIN, NECON, and TRI-NORINYL, from Ortho-McNeil under the tradenames MODICON and ORTHO-NOVUM, and from Warner Chilcott Laboratories, Rockaway, N.J., under the tradename OVCON;

(f) the combination of norgestrel ((±)-13-ethyl-17-hydroxy-18, 19-dinor-17α-preg-4-en-20-yn-3-one) and ethinyl estradiol; available from Wyeth-Ayerst under the tradenames OVRAL and LO/OVRAL, and from Watson under the tradenames OGESTREL and LOW-OGESTREL;

(g) the combination of norethindrone, ethinyl estradiol, and mestranol (3-methoxy-19-nor-17α-pregna-1,3,5(10)-trien-20-yn-17-ol); available from Watson under the tradenames BREVICON and NORINYL;

(h) the combination of 17β-estradiol (estra-1,3,5(10)-triene-3,17β-diol) and micronized norgestimate (17α-17-(Acetyloxy)-13-ethyl- 18,19-dinorpregn-4-en-20-yn-3-one3-oxime); available from Ortho-McNeil under the tradename ORTHO-PREFEST;

(i) the combination of norgestimate (18,19-dinor-17-pregn-4-en-20-yn-3-one, 17-(acetyloxy)-13-ethyl-,oxime, (17(α)-(+)−) and ethinyl estradiol; available from Ortho-McNeil under the tradenames ORTHO CYCLEN and ORTHO TRI-CYCLEN; and j) the combination of conjugated estrogens (sodium estrone sulfate and sodium equilin sulfate) and medroxyprogesterone acetate (20-dione, 17-(acetyloxy)-6-methyl-, (6(α))-pregn-4-ene-3); available from Wyeth-Ayerst under the tradenames PREMPHASE and PREMPRO.

In general, a dosage of progestins may vary from about 0.05 mg to about 10 mg or up to about 200 mg if microsized progesterone is administered. Examples of progestins include norethindrone; available from ESI Lederle, Inc., Philadelphia, Pa., under the tradename AYGESTIN, from Ortho-McNeil under the tradename MICRONOR, and from Watson under the tradename NOR-QD; norgestrel; available from Wyeth-Ayerst under the tradename OVRETTE; micronized progesterone (pregn-4-ene-3, 20-dione); available from Solvay under the tradename PROMETRIUM; and medroxyprogesterone acetate; available from Pharmacia & Upjohn under the tradename PROVERA.

The compositions, therapeutic combinations or methods of the present invention can further comprise one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxtine); thermogenic agents (such as ephedrine, caffeine, theophylline, and selective β3-adrenergic agonists); an alpha-blocking agent; a kainite or AMPA receptor antagonist; a leptin-lipolysis stimulated receptor; a phosphodiesterase enzyme inhibitor; a compound having nucleotide sequences of the mahogany gene; a fibroblast growth factor-10 polypeptide; a monoamine oxidase inhibitor (such as befloxatone, moclobemide, brofaromine, phenoxathine, esuprone, befol, toloxatone, pirlindol, amiflamine, sercloremine, bazinaprine, lazabemide, milacemide and caroxazone); a compound for increasing lipid metabolism (such as evodiamine compounds); and a lipase inhibitor (such as orlistat). Generally, a total dosage of the above-described obesity control medications can range from 1 to 3,000 mg/day, desirably from about 1 to 1,000 mg/day and more desirably from about 1 to 200 mg/day in single or 2–4 divided doses.

The compositions, therapeutic combinations or methods of the present invention can further comprise one or more blood modifiers. Useful blood modifiers include but are not limited to anti-coagulants (argatroban, bivalirudin, dalteparin sodium, desirudin, dicumarol, lyapolate sodium, nafamostat mesylate, phenprocoumon, tinzaparin sodium, warfarin sodium); antithrombotic (anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab, zolimomab aritox); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate, epoprostenol, epoprostenol sodium, ticlopidine hydrochloride, aspirin, ibuprofen, naproxen, sulindae, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitor; Factor VIIa inhibitors (4H-31-benzoxazin-4-ones, 4H-3,1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl} amide trifluoroacetate, dibenzofuran-2-sulfonic acid {1-[3-(aminomethyl)-benzyl]-5-oxo-pyrrolidin-3-yl}-amide, toluene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl )-benzyl]-2-oxo-pyrrolin-3-(S )-yl}-amide trifluoroacetate); Factor Xa inhibitors (disubstituted pyrazolines, disubstituted triazolines, substituted n-[(aminoiminomethyl)phenyl]propylamides, substituted n-[(aminomethyl)phenyl]propylamides, tissue factor pathway inhibitor (TFPI), low molecular weight heparins, heparinoids, benzimidazolines, benzoxazolinones, benzopiperazinones, indanones, dibasic (amidinoaryl) propanoic acid derivatives, amidinophenyl-pyrrolidines, amidinophenyl-pyrrolines, amidinophenyl-isoxazolidines, amidinoindoles, amidinoazoles, bis-arylsulfonylaminobenzamide derivatives, peptidic Factor Xa inhibitors).

The compositions, therapeutic combinations or methods of the present invention can further comprise one or more cardiovascular agents. Useful cardiovascular agents include but are not limited to calcium channel blockers (clentiazem maleate, amlodipine besylate, isradipine, nimodipine, felodipine, nilvadipine, nifedipine, teludipine hydrochloride, diltiazem hydrochloride, belfosdil, verapamil hydrochloride, fostedil); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate, nebivolol); adrenergic stimulants; angiotensin converting enzyme (ACE) inhibitors (benazepril hydrochloride, benazeprilat, captopril, delapril hydrochloride, fosinopril sodium, libenzapril, moexipril hydrochloride, pentopril, perindopril, quinapril hydrochloride, quinaprilat, ramipril, spirapril hydrochloride, spiraprilat, teprotide, enalapril maleate, lisinopril, zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate, bevantolol hydrochloride); angiotensin II receptor antagonists (candesartan, irbesartan, losartan potassium, candesartan cilexetil, telmisartan); anti-anginal agents (amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochoride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexiline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the present invention can further comprise one or more antidiabetic medications for reducing blood glucose levels in a human. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguanide (such as metformin and buformin), thiazolidinedione (such as troglitazone, rosiglitazone, pioglitazone, ciglitazone, englitazone, and darglitazone), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 2–4 divided doses.

Mixtures of any of the pharmacological or therapeutic agents described above can be used in the compositions and therapeutic combinations of these other embodiments of the present invention.

The compositions and therapeutic combinations of the present invention can be administered to a mammal in need of such treatment in a therapeutically effective amount to treat conditions such as xanthomas. The compositions and treatments can be administered by any suitable means that produce contact of these compounds with the site of action in the body, for example in the plasma, liver or small intestine of a mammal or human.

The daily dosage for the various compositions and therapeutic combinations described above can be administered to a patient in a single dose or in multiple subdoses, as desired. Subdoses can be administered 2 to 6 times per day, for example. Sustained release dosages can be used. Where the sterol absorption inhibitor(s) and other therapeutic agent are administered in separate dosages, the number of doses of each component given per day may not necessarily be the same, e.g., one component may have a greater duration of activity and will therefore need to be administered less frequently.

The compositions, therapeutic combinations or medicaments of the present invention can further comprise one or more pharmaceutically acceptable carriers, one or more excipients and/or one or more additives. The pharmaceutical compositions can comprise about 1 to about 99 weight percent of active ingredient (one or more compounds of Formula I–XII), and preferably about 5 to about 95 percent active ingredient.

Useful pharmaceutically acceptable carriers can be solid, liquid or gas. Non-limiting examples of pharmaceutically acceptable carriers include solids and/or liquids such as magnesium carbonate, magnesium stearate, talc, sugar, lactose, ethanol, glycerol, water and the like. The amount of carrier in the treatment composition or therapeutic combination can range from about 5 to about 99 weight percent of the total weight of the treatment composition or therapeutic combination. Non-limiting examples of suitable pharmaceutically acceptable excipients and additives include non-toxic compatible fillers, binders such as starch, polyvinyl pyrrolidone or cellulose ethers, disintegrants such as sodium starch glycolate, crosslinked polyvinyl pyrrolidone or croscarmellose sodium, buffers, preservatives, anti-oxidants, lubricants, flavorings, thickeners, coloring agents, wetting agents such as sodium lauryl sulfate, emulsifiers and the like. The amount of excipient or additive can range from about 0.1 to about 95 weight percent of the total weight of the treatment composition or therapeutic combination. One skilled in the art would understand that the amount of carrier(s), excipients and additives (if present) can vary. Further examples of pharmaceutically acceptable carriers and methods of manufacture for various compositions can be found in A. Gennaro (ed.), Remington: The Science and Practice of Pharmacy, 20$^{th}$ Edition, (2000), Lippincott Williams & Wilkins, Baltimore, Md.

Useful solid form preparations include powders, tablets, dispersible granules, capsules, cachets and suppositories. An example of a preparation of a preferred solid form dosage formulation is provided below.

Useful liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also useful are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

In another embodiment, the present invention provides the use of at least one compound represented by Formulae (I–XII) for manufacture of a medicament (such as one of the compositions discussed above) for the treatment of xanthomas.

The following formulation exemplifies a dosage form of this invention. In the formulation, the term "Active Compound I" designates a sterol or 5α-stanol absorption inhibitor described herein above.

EXAMPLE

| | Tablets | |
|---|---|---|
| No. | Ingredient | mg/tablet |
| 1 | Active Compound I | 10 |
| 2 | Lactose monohydrate NF | 55 |
| 3 | Microcrystalline cellulose NF | 20 |
| 4 | Povidone USP (K29-32) | 4 |
| 5 | Croscarmellose sodium NF | 8 |
| 6 | Sodium lauryl sulfate NF | 2 |
| 7 | Magnesium stearate NF | 1 |
| | Total | 100 |

Method of Manufacture

Mix Item No. 4 with purified water in suitable mixer to form binder solution. Spray the binder solution and then water over Items 1, 2 and 6 and a portion of item 5 in a fluidized bed processor to granulate the ingredients. Continue fluidization to dry the damp granules. Screen the dried granule and blend with Item No. 3 and the remainder of Item No. 5. Add Item No. 7 and mix. Compress the mixture to appropriate size and weight on a suitable tablet machine.

For coadministration in separate tablets or capsules, representative formulations comprising a sterol absorption inhibitor such as are discussed above are well known in the art and representative formulations comprising an additional treatment such as a cholesterol biosynthesis inhibitor discussed above are well known in the art. It is contemplated that where the two active ingredients are administered as a single composition, the dosage forms disclosed above for a sterol absorption inhibitor may readily be modified using the knowledge of one skilled in the art.

Since the present invention relates to reducing the size or number of xanthomas by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one sterol absorption inhibitor and a separate pharmaceutical composition comprising at least one additional treatment described above The kit will preferably include directions for the administration of the separate components. The kit form is particularly advantageous when the separate components must be administered in different dosage forms. (e.g., oral and parenteral) or are administered at different dosage intervals.

The treatment compositions and therapeutic combinations of the present invention can prevent or reduce the incidence, size or number of xanthomas, inhibit the intestinal absorption of cholesterol in mammals, and can be useful in the treatment and/or prevention of vascular conditions, such as atherosclerosis, hypercholesterolemia and sitosterolemia, vascular inflammation, stroke, obesity and lowering of plasma levels of cholesterol in subjects, in particular in humans. As used herein, "vascular" means relating to blood vessels, including but not limited to arteries and/or veins, and includes cardiovascular, cerebrovascular, peripheral vascular and combinations thereof.

In another embodiment of the present invention, the compositions and therapeutic combinations of the present invention can reduce xanthomas by reducing was washed sequentially with NaOH (10%), NaCl (sat'd) and water. The organic layer was dried over $MgSO_4$ and concentrated to obtain a semicrystalline product.

Step 2): To a solution of $TiCl_4$ (18.2 ml, 0.165 mol) in $CH_2Cl_2$ (600 ml) at 0° C., was added titanium isopropoxide (16.5 ml, 0.055 mol). After 15 min, the product of Step 1 (49.0 g, 0.17 mol) was added as a solution in $CH_2Cl_2$ (100 ml). After 5 min., diisopropylethylamine (DIPEA) (65.2 ml, 0.37 mol) was added and the reaction mixture was stirred at 0° C. for 1 h, the reaction mixture was cooled to −20° C., and 4-benzyloxybenzylidine(4-fluoro)aniline (114.3 g, 0.37 mol) was added as a solid. The reaction mixture was stirred vigorously for 4 h at −20° C., then acetic acid was added as a solution in $CH_2Cl_2$ dropwise over 15 min, the reaction mixture was allowed to warm to 0° C., and $H_2SO_4$ (2N) was added. The reaction mixture was stirred an additional 1 h, the layers were separated, washed with water, separated and the organic layer was dried. The crude product was crystallized from ethanol/water to obtain the pure intermediate.

Step 3): To a solution of the product of Step 2 (8.9 g, 14.9 mmol) in toluene (100 ml) at 50° C., was added N,O-bis (trimethylsilyl)acetamide (BSA) (7.50 ml, 30.3 mmol). After 0.5 h, solid TBAF (0.39 g, 1.5 mmol) was added and the reaction mixture stirred at 50° C. for an additional 3 h. The reaction mixture was cooled to 22° C., $CH_3OH$ (10 ml), was added. The reaction mixture was washed with HCl (1N), $NaHCO_3$ (1N) and NaCl (sat'd.), and the organic layer was dried over $MgSO_4$.

Step 4): To a solution of the product of Step 3 (0.94 g, 2.2 mmol) in $CH_3OH$ (3 ml), was added water (1 ml) and $LiOH.H_2O$ (102 mg, 2.4 mmole). The reaction mixture was stirred at 22° C. for 1 h and then additional $LiOH.H_2O$ (54 mg, 1.3 mmole) was added. After a total of 2 h, HCl (1N) and EtOAc was added, the layers were separated, the organic layer was dried and concentrated in vacuo. To a solution of the resultant product (0.91 g, 2.2 mmol) in $CH_2Cl_2$ at 22° C., was added ClCOCOCl (0.29 ml, 3.3 mmol) and the mixture stirred for 16 h. The solvent was removed in vacuo.

Step 5): To an efficiently stirred suspension of 4-fluorophenylzinc chloride (4.4 mmol) prepared from 4-fluorophenylmagnesium bromide (1M in THF, 4.4 ml, 4.4 mmol) and $ZnCl_2$ (0.6 g, 4.4 mmol) at 4° C., was added tetrakis(triphenyl-phosphine)palladium (0.25 g, 0.21 mmol) followed by the product of Step 4 (0.94 g, 2.2 mmol) as a solution in THF (2 ml). The reaction was stirred for 1 h at 0° C. and then for 0.5 h at 22° C. HCl (1N, 5 ml) was added and the mixture was extracted with EtOAc. The organic layer was concentrated to an oil and purified by silica gel chromatography to obtain 1-(4-fluorophenyl)-4(S)-(4-hydroxyphenyl)-3(R)-(3-oxo-3-phenylpropyl)-2-azetidinone:

HRMS calc'd for $C_{24}H_{19}F_2NO_3$=408.1429, found 408.1411.

Step 6): To the product of Step 5 (0.95 g, 1.91 mmol) in THF (3 ml), was added (R)-tetrahydro-1-methyl-3,3-diphenyl-1H,3H-pyrrolo-[1,2-c][1,3,2]oxazaborole (120 mg, 0.43 mmol) and the mixture was cooled to −20° C. After 5 min, borohydride-dimethylsulfide complex (2M in THF, 0.85 ml, 1.7 mmol) was added dropwise over 0.5 h. After a total of 1.5 h, $CH_3OH$ was added followed by HCl (1N) and the reaction mixture was extracted with EtOAc to obtain 1-(4-fluorophenyl)-3(R)-[3(S)-(4-fluorophenyl)-3-hydroxypropyl)]-4(S)-[4-(phenylmethoxy)phenyl]-2-azetidinone (compound 6A-1) as an oil. $^1$ H in $CDCl_3$ d H3 =4.68. J=2.3 Hz. Cl(M$^+$H) 500.

Use of (S)-tetra-hydro-1-methyl-3,3-diphenyl-1H,3H-pyrrolo-[1,2-c][1,3,2]oxazaborole gives the corresponding 3(R)-hydroxypropyl azetidinone (compound 6B-1). $^1$ H in $CDCl_3$ d H3=4.69. J=2.3 Hz. Cl(M$^+$H) 500.

To a solution of compound 6A-1 (0.4 g, 0.8 mmol) in ethanol (2 ml), was added 10% Pd/C (0.03 g) and the reaction mixture was stirred under a pressure (60 psi) of $H_2$ gas for 16 h. The reaction mixture was filtered and the solvent was concentrated to obtain compound 6A. Mp 164–166° C.; Cl(M$^+$H) 410. $[\alpha]_D^{25}$=−28.1° (c 3, $CH_3OH$). Elemental analysis calc'd for $C_{24}H_{21}F_2NO_3$: C70.41; H 5.17; N 3.42; found C 70.25; H 5.19; N 3.54.

Similarly treat compound 6B-1 to obtain compound 6B. Mp 129.5–132.5° C.; Cl(M$^+$H) 410. Elemental analysis calc'd for $C_{24}H_{21}F_2NO_3$: C 70.41; H 5.17; N 3.42; found C 70.30; H 5.14; N 3.52.

Step 6' (Alternative): To a solution of the product of Step 5 (0.14 g, 0.3 mmol) in ethanol (2 ml), was added 10% Pd/C (0.03 g) and the reaction was stirred under a pressure (60 psi) of $H_2$ gas for 16 h. The reaction mixture was filtered and the solvent was concentrated to afford a 1:1 mixture of compounds 6A and 6B.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of decreasing the incidence of xanthoma in a subject comprising the step of administering to a subject in need of such treatment an effective amount of a combination of (i) at least one sterol absorption inhibitor, at least one 5α-stanol absorption inhibitor, or a pharmaceutically acceptable salt or solvate thereof and (ii) at least one HMG-CoA reductase inhibitor as a cholesterol biosynthesis inhibitor, to decrease the incidence of xanthoma in the subject, wherein the at least one sterol or 5α-stanol absorption inhibitor is represented by Formula (I):

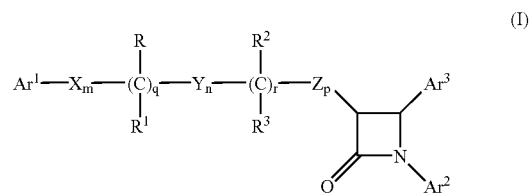

or a pharmaceutically acceptable salt thereof or a solvate thereof, wherein:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(dilower alkyl)-;

R and $R^2$ are independently selected from the group consisting of —$OR^6$, —O(CO)$R^6$, —O(CO)$OR^9$ and —O(CO)$NR^6R^7$;

$R^1$ and $R^3$ are independently selected from the group consisting of hydrogen, lower alkyl and aryl;

q is 0 or 1;

r is 0 or 1;

m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1–5 substituents independently selected from the group consisting of lower alkyl, —$OR^6$, —O(CO)$R^6$, —O(CO)$OR^9$, —O($CH_2$)$_{1-5}$$OR^6$, —O(CO)$NR^6R^7$, —$NR^6R^7$, —$NR^6$(CO)$R^7$, —$NR^6$(CO)$OR^9$, —$NR^6$(CO)$NR^7R^8$, —$NR^6SO_2R^9$, —COO$R^6$, —CON$R^6R^7$, —CO$R^6$, —$SO_2NR^6R^7$, $S(O)_{0-2}R^9$, —O($CH_2$)$_{1-10}$—COO$R^6$, —O($CH_2$)$_{1-10}$CON$R^6R^7$, -(lower alkylene)COO$R^6$, —CH=CH—COO$R^6$, —$CF_3$, —CN, —$NO_2$ and halogen;

$R^5$ is 1–5 substituents independently selected from the group consisting of —$OR^6$, —O(CO)$R^6$, —O(CO)$OR^9$, —O($CH_2$)$_{1-5}$$OR^6$, —O(CO)$NR^6R^7$, —$NR^6R^7$, —$NR^6$(CO)$R^7$, —$NR^6$(CO)$OR^9$, —$NR^6$(CO)$NR^7R^8$, —$NR^6SO_2R^9$, —COO$R^6$, —CON$R^6R^7$, —CO$R^6$, —$SO_2NR^6R^7$, $S(O)_{0-2}R^9$, —O($CH_2$)$_{1-10}$—COO$R^6$, —O($CH_2$)$_{1-10}$CON$R^6R^7$, -(lower alkylene)COO$R^6$ and —CH=CH—COO$R^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

2. The method according to claim 1, wherein the HMG-CoA reductase inhibitor is selected from the group consisting of pravastatin, lovastatin, simvastatin, fluvastatin, rivastatin, rosuvastatin, atorvastatin, cerivastatin, and combinations thereof.

* * * * *